United States Patent
Brookings et al.

(10) Patent No.: US 7,456,286 B2
(45) Date of Patent: *Nov. 25, 2008

(54) BICYCLIC HETEROAROMATIC COMPOUNDS AS KINASE INHIBITORS

(75) Inventors: Daniel Christopher Brookings, Reading (GB); Rachel Jane Cubbon, Slough (GB); Jeremy Martin Davis, Wokingham (GB); Barry John Langham, Reading (GB)

(73) Assignee: UCB Pharma, S.A., Brusseles (BE)

( * ) Notice: Subject to any disclaimer, the term of this patent is extended or adjusted under 35 U.S.C. 154(b) by 394 days.

This patent is subject to a terminal disclaimer.

(21) Appl. No.: 10/529,413

(22) PCT Filed: Sep. 30, 2003

(86) PCT No.: PCT/GB03/04214

§ 371 (c)(1), (2), (4) Date: Jun. 23, 2005

(87) PCT Pub. No.: WO2004/031188

PCT Pub. Date: Apr. 15, 2004

(65) Prior Publication Data

US 2006/0122212 A1    Jun. 8, 2006

(30) Foreign Application Priority Data

Oct. 1, 2002   (GB) ................................ 0222743.7

(51) Int. Cl.
*C07D 471/02* (2006.01)
*A01N 43/90* (2006.01)
(52) U.S. Cl. ...................................... 546/113; 514/300
(58) Field of Classification Search ................ 546/113; 514/300

See application file for complete search history.

(56) References Cited

U.S. PATENT DOCUMENTS 7,176,215 B2 *  2/2007 Davis et al. .................. 514/300
2006/0025428 A1 *  2/2006 Brookings et al. ....... 514/260.1

OTHER PUBLICATIONS

Andresen et al Tetrahedron 52, 12979-12992.*

* cited by examiner

*Primary Examiner*—Rita Desai
*Assistant Examiner*—John Mabry
(74) *Attorney, Agent, or Firm*—McDonnell Boehnen Hulbert & Berghoff LLP

(57) ABSTRACT

A series of 5-6 fused ring bicyclic heteroaromatic derivatives, based in particular on the 5-oxo-4,5-dihydro-1H-pyrrolo[3,2-b]pyridine ring system, being inhibitors of p38 kinase, are accordingly of use in medicine, for example in the treatment and/or prevention of immune or inflammatory disorders.

4 Claims, No Drawings

BICYCLIC HETEROAROMATIC COMPOUNDS AS KINASE INHIBITORS

This invention relates to a series of 5-6 fused ring bicyclic heteroaromatic derivatives, to compositions containing them, to processes for their preparation and to their use in medicine.

Immune and inflammatory responses involve a variety of cell types with control and co-ordination of the various interactions occurring via both cell-cell contacts (e.g. integrin interactions with their receptors) and by way of intercellular signalling molecules. A large number of different signalling molecules are involved including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., *Methods in Enzymology (Protein Kinase Classification)*, p. 3, Hunter, T. and Sefton, B. M. eds., vol. 200, Academic Press, San Diego, 1991].

One sub-class of serine/threonine kinases is the mitogen activating protein (MAP) kinases of which there are at least three families which differ in the sequence and size of the activation loop [Adams, J. L. et al., *Progress in Medicinal Chemistry, pp.* 1-60, King, F. D. and Oxford, A. W. eds., vol. 38, Elsevier Science, 2001]: the extracellular regulated kinases (ERKs); the c-Jun $NH_2$ terminal kinases or stress activated kinases (JNKs or SAP kinases); and the p38 kinases, which have a threonine-glycine-tyrosine (TGY) activation motif. Both the JNKs and p38 MAP kinases are primarily activated by stress stimuli including, but not limited to, proinflammatory cytokines, e.g. tumour necrosis factor (TNF) and interleukin-1 (IL-1), ultraviolet light, endotoxin and chemical or osmotic shock.

Four isoforms of p38 have been described (p38α/β/γ/δ). The human p38α enzyme was initially identified as a target of cytokine-suppressive anti-inflammatory drugs (CSAIDs) and the two isoenzymes found were initially termed CSAID binding protein-1 and -2 (CSBP-1 and CSBP-2 respectively) [Lee, J. C. et al., *Nature (London)*, 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al., *Genomics*, 1995, 29, 301-2]. CSBP-1 and p38α are expressed ubiquitously and there is no difference between the two isoforms with respect to tissue distribution, activation profile, substrate preference or CSAID binding. A second isoform is p38δ which has 70% identity with p38α. A second form of p38δ termed p38β2 is also known and of the two this is believed to be the major form p38α and p38β2 are expressed in many different tissues. However, in monocytes and macrophages p38α is the predominant kinase activity [Lee, J. C., ibid; Jing, Y. et al., *J. Biol. Chem.*, 1996, 271, 10531-34; Hale, K. K. et al., *J. Immun.*, 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al., *FEBS Lett.*, 1995, 364, 7095-8012]. This dual phosphorylation is effected by MKK6 and, under certain conditions, the related enzyme MKK3 [Enslen, H. et al., *J. Biol. Chem.*, 1998, 273, 1741-48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of MAPKKs. MEKK4/MTK1 is thought to be activated by several GADD-45-like genes that are induced in response to environmental stimuli and which eventually lead to p38 activation [Takekawa, M. and Saito, H., *Cell*, 1998, 95, 521-30]. TAK1 has been shown to activate MKK6 in response to transforming growth factor-β (TGF-β). NF-stimulated activation of p38 is believed to be mediated by the recruitment of TRAF2 (TNF receptor associated factor) and the Fas adaptor protein, Daxx, which results in the activation of ASK1 and subsequently p38.

Several substrates of p38 have been identified including other kinases [e.g. MAPK activated protein kinase 2/3/5 (MAPKAP 2/3/5), p38 regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)], transcription factors [e.g. activating transcription factor 2/6 (ATF2/6), monocyte-enhancer factor-2A/C (MEF2A/C), C/EBP homologous protein (CHOP), Elk1 and Sap-1a1] and other substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al., *Nature Cell Biol.*, 1999, 1, 94-7]. Further, MAPKAP K2 from embryonic stem cells from p38α null mice was not activated in response to stress and these cells did not produce IL-6 in response to IL-1 [Allen, M. et al., *J. Exp. Med.*, 2000, 191, 859-69]. These results indicate that MAPKAP K2 is not only essential for TNF and IL-1 production but also for signalling induced by cytokines. In addition, MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low μM range [Lee, J. C. et al., *Int. J. Immunopharm.*, 1988, 10, 835] and exhibit activity in animal models which are refractory to cyclooxygenase inhibitors [Lee, J. C. et al., *Annals N.Y. Acad. Sci.*, 1993, 696, 149]. In addition, these small molecule inhibitors are known to decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by such small molecule inhibitors of p38 [Cohen, P., *Trends Cell Biol.*, 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resorption diseases, reperfusion injury, graft vs. host reaction, allograft rejection, adult respiratory distress syndrome, chronic pulmonary inflammatory disease, silicosis, pulmonary sarcoidosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition, IL-1 has been linked to diabetes and pancreatic β cells [Dinarello, C. A., *J. Clinical Immunology*, 1985, 5, 287-97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis, which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte-derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling, and its influence over not only IL-1, TNF and IL-8 production but also the synthesis and/or action of other pro-inflammatory proteins (e.g. IL-6, GM-CSF, COX-2, collagenase and stromelysin), make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger et al., *J. Pharmacol. Exp. Ther.*, 1996, 279, 1453-61; Griswold et al., *Pharmacol. Commun.*, 1996, 7, 323-29].

Certain N,N'-dibenzylated 2-purinones have been described (Andresen et al., *Tetrahedron*, 52, 12979-12992).

The present invention provides a class of compounds which are potent and selective inhibitors of p38 kinase, especially p38α, p38β and p38β2, and splice variants thereof. The compounds in accordance with the present invention are thus of use in medicine, for example in the prophylaxis and treatment of immune or inflammatory disorders.

In addition, the compounds according to the present invention may be used as pharmacological standards for use in the development of new biological tests and in the search for new pharmacological agents. Thus, the compounds according to this invention may be useful as radioligands in assays for detecting compounds capable of binding to the human p38 enzyme.

Thus according to one aspect of the invention we provide a compound of formula (1):

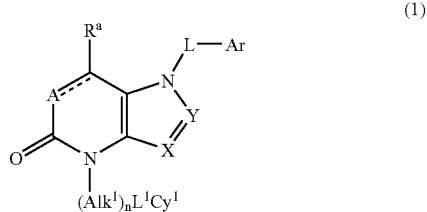

wherein:

the dashed line joining A and C($R^a$) is present and represents a bond and A is a —N= atom or a —C($R^b$)= group, or the dashed line is absent and A is a —C($R^b$)($R^c$)— or —N($R^d$)— group;

$R^a$, $R^b$ and $R^c$ is each independently a hydrogen or halogen atom or an optionally substituted alkyl, —CN, —$CO_2R^1$ (where $R^1$ is a hydrogen atom or an optionally substituted alkyl group) or —$CONR^1R^2$ group (where $R^2$ is a hydrogen atom or an optionally substituted alkyl group);

$R^d$ is a hydrogen atom or an alkyl group;

X and Y is each a nitrogen atom or a —C($R^e$)= or —C($Alk^2R^e$)= group [where $Alk^2$ is an optionally substituted alkylene, alkenylene or alkynylene chain and $R^e$ is a hydrogen or halogen atom or a —CN, —$OR^1$; —$CO_2R^1$, —C($X^a$)$R^1$ (where $X^a$ is an oxygen or sulphur atom), -$Cy^2$ (where $Cy^2$ is an optionally substituted, saturated or unsaturated non-aromatic carbocyclic ring optionally containing one or more —O—, —S—, —NH— or —C($X^a$)— atoms or groups), —$NR^{1a}R^{2a}$ (where $R^{1a}$ and $R^{2a}$, which may be the same or different, is each a hydrogen atom or an optionally substituted alkyl or $Cy^2$ group, or together with the nitrogen atom to which they are attached form an optionally substituted, saturated or unsaturated cyclicamino ring optionally containing one or more —O— or —S— atoms or —NH— or —C($X^a$)— groups), —C($X^a$)$NR^{1a}R^{2a}$, $S(O)_2NR^{1a}R^{2a}$, —N($R^{3a}$)C($X^a$)$R^1$ (where $R^{3a}$ is a hydrogen atom or an optionally substituted alkyl group), —N($R^{3a}$)C($X^a$)$NR^{1a}R^{2a}$, —N($R^{3a}$)$S(O)_2R^1$, —N[$S(O)_2R^1]_2$, —N($R^{3a}$)$S(O)_2$ $NR^{1a}R^{2a}$, —N($R^{3a}$)C(O)$OR^1$, —N($R^{3a}$)C($NR^1$)$NR^{1a}R^{2a}$, —C($R^1$)$NOR^2$, —C($NR^1$)$NR^{1a}R^{2a}$, —C($X^a$)$NR^{1a}OR^{2a}$ or —C(O)N($R^{3a}$)$NR^{1a}R^{2a}$ group];

L is a —C(O)—, —C(S)— or —C($R^{1f}$)($R^{1g}$)— group (where $R^{1f}$ and $R^{1g}$, which may be the same or different, is each a hydrogen atom or a straight or branched $C_{1-3}$alkyl group optionally substituted by one, two or three fluorine atoms, or $R^{1f}$ and $R^{1g}$ together with the carbon atom to which they are attached form a cyclopropyl group), or a —$CH_2CH_2$— group;

n is zero or the integer 1;

$Alk^1$ is an optionally substituted aliphatic or heteroaliphatic chain;

$L^1$ is a covalent bond or a linker atom or group;

$Cy^1$ is an optionally substituted cycloaliphatic, polycycloaliphatic, heterocycloaliphatic, polyheterocycloaliphatic, aromatic or heteroaromatic group, or is additionally a hydrogen atom when n is the integer 1 and/or $L^1$ is a linker atom or group; and Ar is an optionally substituted aromatic or heteroaromatic group;

provided that the compound of formula (1) is other than 3,7-dibenzyl-3,7-dihydro-2H-purinone;

and the salts, solvates, hydrates and N-oxides thereof.

The present invention also provides a compound of formula (1) as depicted above, or a salt, solvate, hydrate or N-oxide thereof, wherein L is a —C(O)—, —C(S)— or —C($R^{1f}$)($R^{1g}$)— group, and the remaining substituents are as defined above.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto ($CH_2C$=O)-enol (CH=CHOH) tautomers. Formula (1) and the formulae hereinafter are intended to represent all individual tautomers and mixtures thereof, unless stated otherwise.

The following general terms as used herein in relation to compounds of the invention and intermediates thereto have the stated meaning below unless specifically defined otherwise.

Thus, as used herein, the term "alkyl" whether present as a group or part of a group includes straight or branched $C_{1-6}$ alkyl groups, for example $C_{1-4}$ alkyl groups such as methyl, ethyl, n-propyl, isopropyl, n-butyl, sec-butyl, isobutyl or tert-butyl groups. Similarly, the terms "alkenyl" and "alkynyl" are intended to mean straight or branched $C_{2-6}$ alkenyl or $C_{2-6}$ alkynyl groups such as $C_{2-4}$ alkenyl or $C_{2-4}$ alkynyl groups.

Optional substituents which may be present on any of these alkyl, alkenyl or alkynyl groups include one, two, three or more substituents where each substituent may be the same or different and is selected from a halogen atom and an —OH, —$CO_2H$, —$CO_2R^4$ (where $R^4$ is an optionally substituted straight or branched $C_{1-6}$ alkyl group), —$CONH_2$, —$CONHR^4$, —$CON(R^4)_2$, —$COR^4$, $C_{1-6}$ alkoxy, halo($C_{1-6}$ alkoxy), —S(O)$R^4$, —S(O)$_2R^4$, $C_{1-6}$ alkylthio, —$NH_2$, —$NHR^4$, —$N(R^4)_2$, —S(O)$_2NH_2$, —S(O)$_2NHR^4$, —S(O)$_2N(R^4)_2$, —NHC(O)$R^4$, —N($R^4$)C(O)$R^4$, —NHS(O)$_2R^4$, —N($R^4$)S(O)$_2R^4$, —NHS(O)$_2NH_2$, —NHS(O)$_2NHR^4$, —NHS(O)$_2N(R^4)_2$, —N($R^4$)S(O)$_2NH_2$, —N($R^4$)S(O)$_2$NH$R^4$ or —N($R^4$)S(O)$_2N(R^4)_2$ group. Where two $R^4$ groups are present in a group, these may be the same or different or may be joined, together with the N atom to which they are attached, to form a heterocyclic ring. Such heterocyclic rings may be optionally interrupted by a further heteroatom or heteroatom-containing group selected from —O—, —S—, —NH—, —N($R^4$)—, —C(O)— and —C(S)— groups. Particular examples of such heterocyclic rings include piperidinyl pyrazolidinyl, morpholinyl, thiomorpholinyl, pyrrolidinyl, imidazolidinyl or piperazinyl rings.

The term "halogen" as used herein is intended to include fluorine, chlorine, bromine and iodine atoms.

The term "haloalkyl" is intended to include those alkyl groups particularly mentioned above substituted by one, two or three of the halogen atoms just described. Particular examples of such groups include —$CF_3$, —$CCl_3$, —$CHF_2$, —$CHCl_2$, —$CH_2F$ and —$CH_2Cl$ groups. Each haloalkyl group may be optionally substituted by one or more hydroxy groups and the term is to be understood to include such substituted groups, such as —C(OH)($CF_3$)$_2$ groups.

The term "alkoxy" as used herein is intended to include straight or branched $C_{1-1}$ alkoxy, e.g. $C_{1-4}$ alkoxy such as methoxy, ethoxy, n-propoxy, isopropoxy, i-butoxy, sec-butoxy, isobutoxy and tert-butoxy. "Haloalkoxy" as used herein includes any of these alkoxy groups substituted by one, two or three halogen atoms as described above. Particular examples include —$OCF_3$, —$OCCl_3$, —$OCHF_2$, —$OCHCl_2$, —$OCH_2F$ and —$OCH_2Cl$ groups.

As used herein, the term "alkylthio" is intended to include straight or branched $C_{1-6}$ alkylthio, e.g. $C_{1-4}$ alkylthio such as methylthio or ethylthio.

When $Alk^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene and $C_{2-6}$ alkynylene chains.

Particular examples of aliphatic chains represented by $Alk^1$ include optionally substituted —$CH_2$—, —$CH_2CH_2$—, —CH($CH_3$)$CH_2$—, —$(CH_2)_2CH_2$—, —$(CH_2)_3CH_2$—, —CH($CH_3$)($CH_2$)$_2CH_2$—, —$CH_2$CH($CH_3$)$CH_2$—, —C($CH_3$)$_2CH_2$—, —$CH_2$C($CH_3$)$_2CH_2$—, —$(CH_2)_2$CH($CH_3$)$CH_2$—, —CH($CH_3$)$CH_2CH_2$—, —CH($CH_3$)$CH_2$CH($CH_3$)$CH_2$—, —$CH_2$CH($CH_3$)$CH_2CH_2$—, —$(CH_2)_2$C($CH_3$)$_2CH_2$—, —$(CH_2)_4CH_2$—, —$(CH_2)_5CH_2$—, —CH=CH—, —CH=CHCH$_2$—, —CH$_2$CH=CH—, —CH=CHCH$_2$CH$_2$—, —CH$_2$CH=CHCH$_2$—, —$(CH_2)_2$CH=CH—, —C≡C—, —C≡CCH$_2$—, —CH$_2$C≡C—, —C≡CCH$_2$CH$_2$—, —CH$_2$C≡CCH$_2$— and —$(CH_2)_2$C≡C— chains.

Heteroaliphatic chains represented by $Alk^1$ in the compounds of formula (1) include the aliphatic chains just described but with each additionally containing one, two, three or four heteroatoms or heteroatom-containing groups. Particular heteroatoms or groups include atoms or groups $L^2$ where $L^2$ is a linker atom or group. Each $L^2$ atom or group may interrupt the aliphatic group, or may be positioned at its terminal carbon atom to connect the group to an adjoining atom or group. Particular examples include optionally substituted -$L^2CH_2$—, —CH$_2L^2$-, -$L^2$CH($CH_3$)—, —CH($CH_3$)$L^2$-, —CH$_2L^2$CH$_2$—, -$L^2$CH$_2$CH$_2$—, -$L^2$CH$_2$CH($CH_3$)—, —CH($CH_3$)CH$_2L^2$-, —CH$_2$CH$_2L^2$-, —CH$_2L^2$CH$_2$CH$_2$—, —CH$_2L^2$CH$_2$CH$_2L^2$-, —$(CH_2)_2L^2$CH$_2$—, —$(CH_2)_3L^2$CH$_2$—, -$L^2(CH_2)_2$CH$_2$—, -$L^2$CH$_2$CH=CH—, —CH=CHCH$_2L^2$- and —$(CH_2)_2L^2$CH$_2$CH$_2$ chains.

When $L^2$ is present in heteroaliphatic chains as a linker atom or group it may be any divalent linking atom or group. Particular examples include —O— or —S— atoms and —C(O)—, —C(O)O—, —OC(O)—, —C(S)—, —S(O)—, —S(O)$_2$—, —N($R^3$)— (where $R^3$ is a hydrogen atom or a straight or branched alkyl group), —N($R^3$)O—, —N($R^3$)NH—, —CON($R^3$)—, —OC(O)N($R^3$)—, —CSN($R^3$)—, —N($R^3$)CO—, —N($R^3$)C(O)O—, —N($R^3$)CS—, —S(O)$_2$N($R^3$)—, —N($R^3$)S(O)$_2$—, —N($R^3$)CON($R^3$)—, —N($R^3$)CSN($R^3$)— or —N($R^3$)SO$_2$N($R^3$)— groups. Where $L^2$ contains two $R^3$ groups these may be the same or different.

The optional substituents which may be present on aliphatic or heteroaliphatic chains represented by $Alk^1$ include one, two or three of those optional substituents described above in relation to the term "alkyl".

When X or Y in compounds of the invention contains an $Alk^2$ chain, the chain may be an optionally substituted, straight or branched $C_{1-6}$ alkylene, $C_{2-6}$ alkenylene or $C_{2-6}$ alkynylene chain. Particular chains include those just described above for the chain $Alk^1$. Where desired, each chain may be substituted by one, two or three substituents as described for $Alk^1$.

When a carbocyclic non-aromatic ring $Cy^2$ is present in compounds of formula (1) it may be an optionally substituted $C_{3-7}$ cycloalkyl, $C_{3-7}$ cycloalkenyl, $C_{3-7}$ heterocycloalkyl or $C_{3-7}$ heterocycloalkenyl ring as generally and particularly described hereinafter in relation to the group $Cy^1$. Optional substituents, which may be present on any available carbon or nitrogen atom in the ring, include those described above in relation to the term "alkyl".

When —$NR^{1a}R^{2a}$ is present in compounds of the invention as a cyclicamino ring it may be an optionally substituted heterocycloaliphatic group, as generally and particularly described below in relation to the group $Cy^1$, which is attached to the remainder of the molecule through a nitrogen atom. Examples include azetidin-1-yl, pyrrolidin-1-yl, piperidin-1-yl, homopiperidin-1-yl, morpholin-4-yl and piperazin-1-yl, especially pyrrolidin-1-yl. Each ring may be optionally substituted on any available ring carbon or nitrogen atom by a substituent selected from those described above in relation to the term "alkyl".

When $L^1$ is present in compounds of formula (1) as a linker atom or group it may be any such atom or group as hereinbefore described in relation to $L^2$ linker atoms and groups.

Optionally substituted cycloaliphatic groups represented by the group $Cy^1$ in compounds of the invention include optionally substituted $C_{3-10}$ cycloaliphatic groups. Particular examples include optionally substituted $C_{3-10}$ cycloalkyl, e.g. $C_{3-7}$ cycloalkyl and $C_{3-10}$ cycloalkenyl, e.g. $C_{3-7}$ cycloalkenyl, groups.

Optionally substituted heterocycloaliphatic groups represented by the group $Cy^1$ include optionally substituted $C_{3-10}$ heterocycloaliphatic groups. Particular examples include optionally substituted $C_{3-10}$ heterocycloalkyl, e.g. $C_{3-7}$ heterocycloalkyl, and $C_{3-10}$ heterocycloalkenyl, e.g. $C_{3-7}$ heterocycloalkenyl, groups, each of said groups containing one, two, three or four heteroatoms or heteroatom-containing groups $L^4$ in place of or in addition to the ring carbon atoms, where $L^4$ is an atom or group as previously defined for $L^2$.

Optionally substituted polycycloaliphatic groups represented by the group $Cy^1$ include optionally substituted $C_{7-10}$ bi- or tricycloalkyl and $C_{7-10}$ bi- or tricycloalkenyl groups. Optionally substituted heteropolycycloaliphatic groups represented by the group $Cy^1$ include optionally substituted $C_{7-10}$ bi- or tricycloalkyl and $C_{7-10}$ bi- or tricycloalkenyl groups containing one, two, three, four or more $L^4$ atoms or groups in place of or in addition to the ring carbon atoms.

Particular examples of cycloaliphatic, polycycloaliphatic, heterocycloaliphatic and heteropolycycloaliphatic groups represented by the group $Cy^1$ include optionally substituted cyclopropyl, cyclobutyl cyclopentyl, cyclohexyl, cycloheptyl, cyclobut-2-en-1-yl, cyclopent-2-en-1-yl, cyclopent-3-en-1-yl, adamantyl, norbornyl, norbornenyl, dihydrofuryl tetrahydrofuryl, tetrahydropyranyl, dihydrothienyl, tetrahydrothienyl pyrrolinyl, e.g. 2- or 3-pyrrolinyl, pyrrolidinyl, pyrrolidinonyl, oxazolidinyl, oxazolidinonyl, dioxolanyl, e.g. 1,3-dioxolanyl, imidazolinyl, e.g. imidazolin-2-yl, imidazolidinyl, pyrazolinyl, e.g. pyrazolin-2-yl, pyrazolidinyl, 5,6-dihydro-2(1H)-pyrazinonyl, tetrahydropyrimidinyl, thiazolinyl, thiazolidinyl pyranyl, e.g. 2- or 4-pyranyl piperidinyl, homopiperidinyl, heptamethyleneiminyl piperidinonyl, 1,4-dioxanyl, morpholinyl, morpholinonyl, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5- or 1,2,6-oxathiazinyl, 1,3,5-oxadiazinyl, dihydroisothiazolyl dihydroisothiazole 1,1-dioxide, e.g. 2,3-dihydroisothiazole 1,1-dioxide, dihydropyrazinyl and tetrahydropyrazinyl groups.

The optional substituents which may be present on the cycloaliphatic, polycycloaliphatic, heterocycloaliphatic or heteropolycycloaliphatic groups represented by the group $Cy^1$ include one, two, three or more substituents selected from halogen atoms, and $C_{1-6}$ alkyl e.g. methyl or ethyl, halo($C_{1-6}$)alkyl, e.g. halomethyl or haloethyl such as difluoromethyl or trifluoromethyl, optionally substituted by hydroxy, e.g. —C(OH)(CF$_3$)$_2$, $C_{1-6}$ alkoxy, e.g. methoxy or ethoxy, halo($C_{1-6}$)alkoxy, e.g. halomethoxy or haloethoxy such as difluoromethoxy or trifluoromethoxy, thiol, $C_{1-6}$ alkylthio, e.g. methylthio or ethylthio, carbonyl (=O), thiocarbonyl (=S), imino (=$NR^{4a}$) (where $R^{4a}$ is an —OH group or a $C_{1-6}$ alkyl group) or -(Alk$^3$)$_v$R$^5$ groups, in which Alk$^3$ is a straight or branched $C_{1-3}$ alkylene chain, v is zero or the integer 1, and $R^5$ is a $C_{3-8}$ cycloalkyl, —OH, —SH, —N(R$^6$)(R$^7$) (in which $R^6$ and $R^7$ is each independently selected from a hydrogen atom and an optionally substituted alkyl or $C_{3-8}$ cycloalkyl group), —OR$^6$, —SR$^6$, —CN, —NO$_2$, —CO$_2$R$^6$, —SOR$^6$, —SO$_2$R$^6$, —SO$_3$R$^6$, —OCO$_2$R$^6$, —C(O)R$^6$, —OC(O)R$^6$, —C(S)R$^6$, —C(O)N(R$^6$)(R$^7$), —OC(O)N(R$^6$)(R$^7$), —N(R)C(O)R$^7$, —C(S)N(R)(R$^7$), —N(R$^6$)C(S)R$^7$, —SO$_2$N(R$^6$)(R$^7$), —N(R$^6$)SO$_2$R$^7$, —N(R$^6$)C(O)N(R$^7$)(R$^8$) (where R$^8$ is as defined for R$^6$), —N(R$^6$)C(S)N(R$^7$)(R$^8$) or —N(R$^6$)SO$_2$N(R$^7$)(R$^8$) group, or an optionally substituted aromatic or heteroaromatic group.

Particular examples of Alk$^3$ chains include —CH$_2$—, —CH$_2$CH$_2$—, —CH$_2$CH$_2$CH$_2$— and —CH(CH$_3$)CH$_2$— chains.

When R$^5$, R$^6$, R$^7$ and/or R$^8$ is present as a $C_{3-8}$ cycloalkyl group it may be, for example, a cyclopropyl, cyclobutyl, cyclopentyl or cyclohexyl group. Optional substituents which may be present on such groups include, for example, one, two or three substituents, which may be the same or different, selected from halogen atoms, for example fluorine, chlorine, bromine or iodine atoms, and hydroxy or $C_{1-6}$ alkoxy groups, e.g. methoxy, ethoxy or isopropoxy groups.

When the groups R$^6$ and R$^7$ or R$^7$ and R$^8$ are both alkyl groups these groups may be joined, together with the N atom to which they are attached, to form a heterocyclic ring. Such heterocyclic rings may be optionally interrupted by a further heteroatom or heteroatom-containing group selected from —O—, —S—, —N(R$^7$)—, —C(O)— and —C(S)— groups. Particular examples of such heterocyclic rings include piperidinyl, pyrazolidinyl, morpholinyl, thiomorpholinyl; pyrrolidinyl, imidazolidinyl and piperazinyl rings.

When R$^5$ is an optionally substituted aromatic or heteroaromatic group it may be any such group as described hereinafter in relation to Cy$^1$.

Additionally, when the group Cy$^1$ is a heterocycloaliphatic or heteropolycycloaliphatic group containing one or more nitrogen atoms each nitrogen atom may be optionally substituted by a group -(L$^5$)$_p$(Alk$^4$)$_q$R$^9$ in which L$^5$ is a —C(O)—, —C(O)O—, —C(S)—, —S(O)$_2$—, —CON(R$^6$)— or —SO$_2$N(R$^6$)— group; p is zero or the integer 1; Alk$^4$ is an optionally substituted aliphatic or heteroaliphatic chain; q is zero or the integer 1; and R$^9$ is a hydrogen atom or an optionally substituted cycloaliphatic, heterocycloaliphatic, polycycloaliphatic, heteropolycycloaliphatic, aromatic or heteroaromatic group as herein described in relation to Cy$^1$.

When Alk$^4$ is present as an aliphatic or heteroaliphatic chain it may be, for example, any aliphatic or heteroaliphatic chain as hereinbefore described for Alk$^1$.

Optionally substituted aromatic groups represented by the group Cy$^1$ include, for example, monocyclic and bicyclic fused ring $C_{6-12}$ aromatic groups, such as phenyl 1- or 2-naphthyl 1- or 2-tetrahydronaphthyl, indanyl or indenyl groups.

Heteroaromatic groups represented by the group $Cy^1$ include, for example, $C_{1-9}$ heteroaromatic groups containing, for example, one, two, three or four heteroatoms selected from oxygen, sulphur and nitrogen atoms. In general, the heteroaromatic groups may be, for example, monocyclic or bicyclic fused ring heteroaromatic groups. Monocyclic heteroaromatic groups include, for example, five- or six-membered heteroaromatic groups containing one, two, three or four heteroatoms selected from oxygen, sulphur and nitrogen atoms. Bicyclic heteroaromatic groups include, for example, eight- to thirteen-membered fused ring heteroaromatic groups containing one, two or more heteroatoms selected from oxygen, sulphur and nitrogen atoms.

Particular examples of heteroaromatic groups of these types include pyrrolyl, furyl, thienyl, imidazolyl, N-($C_{1-6}$ alkyl)imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridinyl, pyrimidinyl, pyridazinyl, pyrazinyl, 1,3,5-triazinyl, 1,2,4-triazinyl, 1,2,3-triazinyl, benzofuryl, (2,3-dihydro)benzofuryl, benzothienyl, (2,3-dihydro) benzothienyl, benzotriazolyl, indolyl, indolinyl, indazolinyl, benzimidazolyl, imidazo[1,2-a]pyridinyl, benzothiazolyl, benzoxazolyl, benzisoxazolyl, benzopyranyl, (3,4-dihydro) benzopyranyl, quinazolinyl, quinoxalinyl, naphthyridinyl, imidazo[1,5-a]pyridinyl, imidazo[1,5-a]pyrazinyl, imidazo[1,5-c]pyrimidinyl, pyrido[3,4-b]pyridinyl, pyrido[3,2-b]pyridinyl, pyrido[4,3-b]pyridinyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-d]pyrimidinyl, thieno[3,2-d]pyrimidinyl, pyrrolo[3,2-d]pyrimidinyl, pyrazolo[3,2-b]pyridinyl, furo[3,2-b]pyridinyl, thieno[3,2-b]pyridinyl, pyrrolo[3,2-b]pyridinyl, thiazolo[3,2-a]pyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group $Cy^1$ include one, two, three or more substituents, each selected from an atom or group $R^{10}$ in which $R^{10}$ is $R^{10a}$ or -$L^6Alk^5(R^{10a})_r$, where $R^{10a}$ is a halogen atom, or an amino (—$NH_2$), substituted amino, nitro, cyano, hydroxy (—OH), substituted hydroxy, formyl, carboxy (—$CO_2H$), esterified carboxy, thiol (—SH), substituted thiol, —$COR^{11}$ (where $R^{11}$ is an -$L^6Alk^3$ ($R^{10a})_r$, aryl or heteroaryl group), —$CSR^{11}$, —$SO_3H$, —$SOR^{11}$, —$SO_2R^{11}$, —$SO_3R^{11}$, —$SO_2NH_2$, —$SO_2NHR^{11}$, —$SO_2N(R^{11})_2$, —$CONH_2$, —$CSNH_2$, —$CONHR^{11}$, —$CSNHR^{11}$, —$CON(R^{11})_2$, —$CSN(R^{11})_2$, —$N(R^{12})SO_2R^{11}$ (where $R^{12}$ is a hydrogen atom or a straight or branched alkyl group), —$N(SO_2R^{11})_2$, —$N(R^{12})SO_2NH_2$, —$N(R^{12})SO_2NHR^{11}$, —$N(R^{12})SO_2N(R^{11})_2$, —$N(R^{12})COR^{11}$, —$N(R^{12})CONH_2$, —$N(R^{12})CON(R^{11})$—$N(R^{12})CON(R^{11})_2$, —$N(R^{12})CSNH_2$, —$N(R^{12})CSNHR^{11}$, $N(R^{12})CSN(R^{11})_2$, —$N(R^{12})CSR^{11}$, —$N(R^2)C(O)OR^{11}$, —$SO_2NHet^1$ (where -$Het^2$ is an optionally substituted $C_{5-7}$ cyclic amino group optionally containing one or more other —O— or —S— atoms or —$N(R^{12})$—, —C(O)— or —C(S)— groups), —$CONHet^1$, —$CSNHet^1$, —$N(R^{12})SO_2NHet^1$, —$N(R^{12})CONHet^1$, —$N(R^{12})CSNHet^1$, —$SO_2N(R^{12})Het^2$ (where -$Het^2$ is an optionally substituted monocyclic $C_{5-7}$ carbocyclic group optionally containing one or more other —O— or —S— atoms or —$N(R^{12})$—, —C(O)—, —S(O)— or —$S(O)_2$— groups), -$Het^2$, —$CON(R^{12})Het^2$, $CSN(R^{12})$ $Het^2$, —$N(R^{12})CON(R^{12})Het^2$, —$N(R^{12})CSN(R^{12})Het^2$, —$N(R^{12})SO_2N(R^{12})Het^2$, aryl or heteroaryl group; $L^6$ is a covalent bond or a linker atom or group as hereinbefore defined for $L^2$; $Alk^5$ is an optionally substituted straight or branched $C_{1-6}$ alkylene, $C_{2-6}$ alkenylene or $C_{2-6}$ alkynylene chain, optionally interrupted by one, two or three —O— or —S— atoms or —S(O)—, —$S(O)_2$— or —$N(R^{12})$—, e.g. —$N(CH_3)$—, groups; and r is zero or the integer 1, 2, or 3. It will be appreciated that when two $R^{11}$ or $R^{12}$ groups are present in one of the above substituents the $R^{11}$ and $R^{12}$ groups may be the same or different.

When in the group -$L^6Alk^5(R^{10a})_r$, r is an integer 1, 2 or 3, it is to be understood that the substituent or substituents $R^{10a}$ may be present on any suitable carbon atom in $Alk^5$. Where more than one $R^{10a}$ substituent is present these may be the same or different and may be present on the same atom or on different atoms in $Alk^5$. Clearly, when r is zero and no substituent $R^{10a}$ is present the alkylene, alkenylene or alkynylene chain represented by $Alk^5$ becomes an alkyl, alkenyl or alkynyl group.

When $R^{10a}$ is a substituted amino group it may be, for example, a group —$NHR^{11}$ (where $R^{11}$ is as defined above) or a group —$NR^{11})_2$ wherein each $R^{11}$ group is the same or different.

When $R^{10a}$ is a halogen atom it may be, for example, a fluorine, chlorine, bromine or iodine atom.

When $R^{10a}$ is a substituted hydroxy or substituted thiol group it may be, for example, a group —$OR^{11}$ or —$SR^{12}$ respectively.

Esterified carboxy groups represented by the group $R^{10a}$ include groups of formula —$CO_2Alk^6$ wherein $Alk^6$ is a straight or branched, optionally substituted $C_{1-8}$ alkyl group such as a methyl, ethyl, n-propyl, isopropyl, n-butyl isobutyl, sec-butyl or tert-butyl group; a $C_{6-12}$ aryl($C_{1-8}$ alkyl) group such as an optionally substituted benzyl phenylethyl, phenylpropyl, 1-naphthylmethyl or 2-naphthylmethyl group; a $C_{6-12}$ aryl group such as an optionally substituted phenyl, 1-naphthyl or 2-naphthyl group; a $C_{6-12}$ aryloxy($C_{1-8}$ alkyl) group such as an optionally substituted phenoxymethyl, phenoxyethyl, 1-naphthyloxymethyl or 2-naphthyloxymethyl group; an optionally substituted $C_{1-8}$ alkanoyloxy($C_{1-8}$ alkyl) group, such as a pivaloyloxymethyl, propionyloxyethyl or propionyloxypropyl group; or a $C_{6-12}$ aroyloxy($C_{1-8}$ alkyl) group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be, for example, a —$CH_2$—, —$CH(CH_3)$—, $C(CH_3)_2$—, —$CH_2CH_2$—, —$CH_2CH_2CH_2$—, —$CH(CH_3)CH_2$—, —$CH_2CH_2CH_2CH_2$—, —$CH_2CH(CH_3)CH_2$—, —CH($CH_3$)$CH_2CH_2$—, —C($CH_3)_2CH_2$—, —CH=CH—, —CH=$CHCH_2$—, —$CH_2CH$=CH—, —CH=$CHCH_2CH_2$—, —$CH_2CH$=$CHCH_2$—, —$CH_2CH_2CH$=CH—, —C≡C—, —C≡$CCH_2$—, —$CH_2C$≡C—, —C≡$CCH_2CH_2$—, —$CH_2C$≡$CCH_2$— or —$CH_2CH_2C$≡C— chain, optionally interrupted by one, two or three —O— or —S— atoms or —S(O)—, —$S(O)_2$— or —$N(R^{12})$—, e.g. —$N(CH_3)$—, groups. The aliphatic chains represented by $Alk^5$ may be optionally substituted by one, two or three halogen atoms in addition to any $R^{10a}$ groups that may be present.

Aryl or heteroaryl groups represented by the groups $R^{10a}$ or $R^{11}$ include mono- and bicyclic optionally substituted $C_{6-12}$ aromatic or $C_{1-9}$ heteroaromatic groups as described above for the group $Cy^1$. The aromatic and heteroaromatic groups may be attached to the group $Cy^1$ in compounds of formula (1) by any carbon atom or heteroatom, e.g. nitrogen atom, as appropriate.

It will be appreciated that when —$NHet^1$ or -$Het^2$ forms part of a substituent $R^{10}$ the heteroatoms or heteroatom-containing groups that may be present within the ring —NHet$^1$ or -Het$^2$ take the place of carbon atoms within the parent carbocyclic ring.

Thus, when —NHet$^1$ or -Het$^2$ forms part of a substituent R$^{10}$ each may be, for example, an optionally substituted pyrrolidinyl, imidazolidinyl, pyrazolinyl, piperazinyl, morpholinyl, thiomorpholinyl, piperidinyl or thiazolidinyl group. Additionally, -Het$^2$ may represent, for example, an optionally substituted cyclopentyl or cyclohexyl group. Optional substituents which may be present on —NHet$^1$ include those substituents described above when Cy$^1$ is a heterocycloaliphatic group.

Particularly useful atoms or groups represented by R$^{10}$ include fluorine, chlorine, bromine or iodine atoms, and $C_{1-6}$ alkyl, e.g. methyl ethyl, n-propyl isopropyl, n-butyl or tert-butyl optionally substituted phenyl, pyridinyl, pyrimidinyl, pyrrolyl furyl, thiazolyl or thienyl, $C_{1-6}$ hydroxyalkyl, e.g. hydroxymethyl or hydroxyethyl carboxy($C_{1-6}$ alkyl), e.g. carboxyethyl, $C_{1-6}$ alkylthio, e.g. methylthio or ethylthio, carboxy($C_{1-6}$ alkyl)thio, e.g. carboxymethylthio, 2-carboxyethylthio or 3-carboxypropylthio, $C_{1-6}$ alkoxy, e.g. methoxy or ethoxy, hydroxy($C_{1-6}$ alkoxy), e.g. 2-hydroxyethoxy, optionally substituted phenoxy, pyridinyloxy, thiazolyloxy, phenylthio or pyridinylthio, $C_{3-7}$ cycloalkyl, e.g. cyclobutyl or cyclopentyl, $C_{5-7}$ cycloalkoxy, e.g. cyclopentyloxy, halo($C_{1-6}$ alkyl), e.g. trifluoromethyl, halo($C_{1-6}$ alkoxy), e.g. trifluoromethoxy, $C_{1-6}$ alkylamino, e.g. methylamino, ethylamino, —CH(CH$_3$)NH$_2$ or —C(CH$_3$)$_2$NH$_2$, halo($C_{1-6}$ alkyl)amino, e.g. fluoro($C_{1-6}$ alkyl)amino such as —CH(CF$_3$)NH$_2$ or —C(CF$_3$)$_2$NH$_2$, amino (—NH$_2$), amino($C_{1-6}$ alkyl), e.g. aminomethyl or aminoethyl, di($C_{1-6}$ alkyl)amino, e.g. dimethylamino or diethylamino, $C_{1-6}$ alkylamino($C_{1-6}$ alkyl), e.g. ethylaminoethyl, di-($C_{1-6}$ alkyl)amino($C_{1-6}$ alkyl), e.g. diethylaminoethyl, amino($C_{1-6}$ alkoxy), e.g. aminoethoxy, $C_{1-6}$ alkylamino($C_{1-6}$ alkoxy), e.g. methylaminoethoxy, di($C_{1-6}$ alkyl)amino($C_{1-6}$ alkoxy), e.g. dimethylaminoethoxy, diethylaminoethoxy, diisopropylaminoethoxy or dimethylaminopropoxy, imido, such as phthalimido or naphthalimido, e.g. 1,8-naphthalimido, nitro, cyano, hydroxy (—OH), formyl [HC(O)—], carboxy (—CO$_2$H), —CO$_2$Alk$^6$ (where Alk$^6$ is as defined above), $C_{1-6}$ alkanoyl, e.g. acetyl, optionally substituted benzoyl, thiol (—SH), thio($C_{1-6}$ alkyl), e.g. thiomethyl or thioethyl, sulphonyl (—SO$_3$H), $C_{1-6}$ alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, di($C_{1-6}$alkyl)aminosulphonyl, e.g. dimethylaminosulphonyl or diethylaminosulphonyl, phenylaminosulphonyl, carboxamido (—CONH$_2$), $C_{1-6}$ alkylaminocarbonyl, e.g. methylaminocarbonyl or ethylaminocarbonyl, di($C_{1-6}$ alkyl)aminocarbonyl, e.g. dimethylaminocarbonyl or diethylaminocarbonyl, amino ($C_{1-6}$ alkyl)aminocarbonyl, e.g. aminoethylaminocarbonyl, di($C_{1-6}$ alkyl)amino($C_{1-6}$ alkyl)aminocarbonyl, e.g. diethylaminoethylaminocarbonyl, aminocarbonylamino, $C_{1-6}$ alkylaminocarbonylamino, e.g. methyl aminocarbonylamino or ethylaminocarbonylamino, di($C_{1-6}$ alkyl)aminocarbonylamino, e.g. dimethylaminocarbonylamino or diethylaminocarbonylamino, $C_{1-6}$ alkylaminocarbonyl($C_{1-6}$ alkyl) amino, e.g. methylaminocarbonylmethylamino, aminothiocarbonylamino, $C_{1-6}$ alkylaminothiocarbonylamino, e.g. methylaminothiocarbonylamino or ethylaminothiocarbonylamino, di($C_{1-6}$ alkylaminothiocarbonylamino, e.g. dimethylaminothiocarbonylamino or diethylaminothiocarbonylamino, $C_{1-6}$ alkylaminothiocarbonyl($C_{1-6}$ alkyl)amino, e.g. ethylaminothiocarbonylmethylamino, —CONHC(=NH)NH$_2$, $C_{1-6}$ alkylsulphonylamino, e.g. methylsulphonylamino or ethylsulphonylamino, di($C_{1-6}$ alkyl)sulphonylamino, e.g. dimethylsulphonylamino or diethylsulphonylamino, optionally substituted phenylsulphonylamino, aminosulphonylamino (—NHSO$_2$NH$_2$), $C_{1-6}$ alkylaminosulphonylamino, e.g. methylaminosulphonylamino or ethylaminosulphonylamino, di($C_{1-6}$ alkyl)aminosulphonylamino, e.g. dimethylamino-sulphonylamino or diethylaminosulphonylamino, optionally substituted morpholinylsulphonylamino or morpholinylsulphonyl($C_{1-6}$ alkyl)amino, optionally substituted phenylaminosulphonylamino, $C_{1-6}$ alkanoylamino, e.g. acetylamino, amino($C_{1-6}$ alkanoyl)amino, e.g. aminoacetylamino, di($C_{1-6}$ alkyl)amino ($C_{1-6}$ alkanoyl)amino, e.g. dimethylaminoacetylamino, $C_{1-6}$ alkanoylamino($C_{1-6}$ alkyl), e.g. acetylaminomethyl, $C_{1-6}$ alkanoylamino($C_{1-6}$ alkyl)amino, e.g. acetamidoethylamino, $C_{1-6}$ alkoxycarbonylamino, e.g. methoxycarbonylamino, ethoxycarbonylamino or tert-butoxycarbonylamino, or optionally substituted benzyloxy, pyridinylmethoxy, thiazolylmethoxy, benzyloxycarbonylamino, benzyloxycarbonylamino($C_{1-6}$ alkyl), e.g. benzyloxycarbonylaminoethyl, benzothio, pyridinylmethylthio or thiazolylmethylthio groups.

A further particularly useful group of substituents represented by R$^{10}$ when present on aromatic or heteroaromatic groups includes substituents of formula -L$^6$Alk$^5$R$^{10a}$ where L$^6$ is preferably a covalent bond, an —O— or —S— atom or a —N(R$^3$)—, —C(O)—, —C(O)O—, —OC(O)—, —N(R$^3$) CO—, —CON(R$^3$)— or —N(R$^3$)S(O)$_2$— group; Alk$^5$ is an optionally substituted $C_{1-6}$ alkylene group optionally interrupted by one or two —O— or —S— atoms or —N(R)—, —C(O)—, —C(S)—, —CON(R$^{12}$)— or —N(R$^{12}$)CO— groups; and R$^{10a}$ is an optionally substituted -Het$^2$ group as herein defined or an optionally substituted heteroaromatic group as hereinbefore described in relation to Cy$^1$.

Where desired, two R$^{10}$ substituents may be linked together to form a cyclic group such as a cyclic ether, e.g. a $C_{1-6}$ alkylenedioxy group such as methylenedioxy or ethylenedioxy.

It will be appreciated that where two or more R$^{10}$ substituents are present, these need not necessarily be the same atoms and/or groups. In general, the substituent(s) may be present at any available ring position on the aromatic or heteroaromatic group represented by the group Cy$^1$.

As used above, the terms "alkylamino" and "dialkylamino" are intended to include the groups —NHR$^{13}$ and —N(R$^{13}$)(R$^{14}$) respectively, where R$^{13}$ and R$^{14}$ is each independently an optionally substituted straight or branched alkyl group or both together with the N atom to which they are attached form an optionally substituted heterocycloalkyl group which may contain a further heteroatom or heteroatom-containing group such as an —O— or —S— atom or an —N(R)— group. Particular examples of such optionally substituted heterocycloalkyl groups include optionally substituted pyrrolidinyl, piperidinyl, morpholinyl, thiomorpholinyl and N'-($C_{1-6}$ alkyl)piperazinyl groups. The optional substituents which may be present on such heterocycloalkyl groups include those optional substituents as described hereinafter in relation to aliphatic chains such as Alk$^1$.

The optionally substituted aromatic or heteroaromatic group represented by Ar in compounds of the invention may be any aromatic or heteroaromatic group as hereinbefore generally or particularly described for Cy$^1$. Optional substituents which may be present include those R$^{10}$ atoms and groups as generally or particularly described in relation to Cy$^1$ aromatic and heteroaromatic groups.

Suitable values of R$^e$ in the compounds of formula (1) above include hydrogen, —CN, —COR$^1$, —CO$_2$R$^1$, CONR$^{1a}$R$^{2a}$, —S(O)$_2$NR$^{1a}$R$^{2a}$, —CONR$^{1a}$OR$^{2a}$ and C(O)N(R$^{3a}$)NR$^{1a}$R$^{2a}$.

Suitably, $R^1$ represents methyl, ethyl or trifluoromethyl. In one embodiment, $R^1$ is ethyl. In another embodiment, $R^1$ is trifluoromethyl.

Suitable values of $R^{1a}$ include hydrogen and methyl.

Suitable values of $R^{2a}$ include hydrogen and methyl.

In a typical embodiment, $R^{1e}$ and $R^{2a}$ together represent —$(CH_2)_4$—. In another embodiment, $R^{1a}$ and $R^{2a}$ together represent —$CH(CH_2OH)(CH_2)_3$—.

Typically, $R^{3a}$ is hydrogen.

Detailed values of $R^e$ include hydrogen, cyano, trifluoroacetyl, ethoxycarbonyl, aminocarbonyl, methylaminocarbonyl, dimethylaminocarbonyl, pyrrolidinylcarbonyl, hydroxymethyl-pyrrolidinylcarbonyl, pyrrolidinylsulphonyl (N-methoxy)(N-methyl)-aminocarbonyl and hydrazinocarbonyl.

In general, in compounds of formula (1) X and Y is each preferably a —$C(R^e)$= or —$C(Alk^2R^e)$= group. $R^e$ in these compounds is especially a hydrogen atom or a —$CONR^{1a}R^{2a}$ or —$S(O)_2NR^{1a}R^{2a}$ group. $Alk^2$ when present is in particular a —$CH_2$— or —$(CH_2)_2$— chain.

In one preference, X is a —CH= group and Y is a —$C(R^e)$= or —$C(Alk^2R^e)$= group, especially where $R^e$ is a hydrogen atom or a —$CONR^{1a}R^{2a}$ or —$S(O)_2NR^{1a}R^{2a}$ group and $Alk^2$ is a —$CH_2$— or —$(CH_2)_2$— chain.

In one group of compounds of formula (1) the bond represented by the dashed line is present and A is a —$C(R^b)$= group. In these compounds $R^b$ is preferably a hydrogen atom or a $C_{1-4}$ alkyl group, especially a methyl, ethyl, n-propyl or isopropyl group. More particularly, $R^b$ is a methyl group or more especially a hydrogen atom.

One particularly useful class of compounds according to the invention has the formula (1) wherein A, X and Y is each a —CH= group and $R^a$, $Alk^1$, n, $L^1$, $Cy^1$, L and Ar are as generally or particularly defined herein; and the salts, solvates, hydrates and N-oxides thereof.

In general, in compounds of formula (1) $R^a$ is preferably a hydrogen atom or a $C_{1-4}$ alkyl group, especially a methyl, ethyl, n-propyl or isopropyl group. In particular, $R^1$ is a methyl group or more especially a hydrogen atom.

When in compounds of formula (1) n is the integer 1, $Alk^1$ is preferably an optionally substituted $C_{1-6}$ alkylene chain, especially an optionally substituted —$CH_2$—, —$CH_2CH_2$—, —$CH_2CH_2CH_2$—, —$CH(CH_3)CH_2$— or —$CH_2CH(CH_3)$— chain, more especially a —$CH_2$— or —$CH_2CH_2$— chain, and most especially a —$CH_2$— chain.

In one class of compounds of formula (1) n is zero.

The group $L^1$ in compounds of formula (1) is preferably a covalent bond, an —O— or —S— atom or an —$N(R^3)$—, especially —NH— or —$N(CH_3)$—, —C(O)—, —C(S)—, —S(O)— or —$S(O)_2$— group. More particularly, $L^1$ is a covalent bond, an —O— or —S— atom or a —NH— group. $L^1$ is most preferably a covalent bond.

$Cy^1$ in compounds of formula (1) is preferably an optionally substituted cycloaliphatic, aromatic or heteroaromatic group as hereinbefore generally and particularly defined.

Particularly preferred $Cy^1$ optionally substituted cycloaliphatic groups include optionally substituted $C_{3-7}$ cycloalkyl groups, especially cyclopropyl, cyclobutyl, cyclopentyl or cyclohexyl groups.

Particularly preferred optional substituents which may be present on $Cy^1$ optionally substituted cycloaliphatic groups include halogen atoms, especially fluorine, chlorine or bromine atoms, $C_{1-6}$ alkyl groups, especially $C_{1-3}$ alkyl groups, most especially a methyl group, halo($C_{1-6}$ alkyl) groups, especially fluoro($C_{1-6}$ alkyl) groups, most especially a —$CF_3$ group, $C_{1-6}$ alkoxy groups, especially a methoxy, ethoxy, propoxy or isopropoxy group, and halo($C_{1-6}$ alkoxy) groups, especially fluoro($C_{1-6}$ alkoxy) groups, most especially a —$OCF_3$ group, or a cyano (—CN), esterified carboxy, especially —$CO_2CH_3$ or —$CO_2C(CH_3)_3$, nitro (—$NO_2$), amino (—$NH_2$), substituted amino, especially —$NHCH_3$ or —$N(CH_3)_2$, —$C(O)R^6$, especially —$C(O)CH_3$, or —$N(R^6)C(O)R^7$, especially —$NHCOCH_3$, group.

Particularly preferred $Cy^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur and nitrogen atoms. Particularly preferred optionally substituted monocyclic heteroaromatic groups include optionally substituted furyl, thienyl, pyrrolyl, oxazolyl, thiazolyl, pyridinyl, pyrimidinyl and triazinyl groups.

Particularly preferred optional substituents which may be present on $Cy^1$ aromatic or heteroaromatic groups include atoms or groups —$R^{10a}$ and -$L^6Alk^5(R^{10a})_r$ as hereinbefore defined. Particularly useful optional substituents include halogen atoms, especially fluorine, chlorine or bromine atoms, $C_{1-6}$ alkyl groups, especially $C_{1-3}$ alkyl groups, most especially a methyl group, halo($C_{1-6}$ alkyl) groups, especially fluoro($C_{1-6}$ alkyl) groups, most especially a —$CF_3$ group, $C_{1-6}$ alkoxy groups, especially a methoxy, ethoxy, n-propoxy or isopropoxy group, and halo($C_{1-6}$ alkoxy) groups, especially fluoro($C_{1-6}$ alkoxy) groups, most especially a —$OCF_3$ group, or a cyano (—CN), carboxy (—$CO_2H$), esterified carboxy (—$CO_2Alk^6$), especially —$CO_2CH_3$, —$CO_2CH_2CH_3$ or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$, group.

Further preferred optional substituents which may be present on $Cy^1$ aromatic or heteroaromatic groups include groups of formula -$L^6Alk^5(R^{10a})_r$ in which r is the integer 1; $L^6$ is a covalent bond, an —O— or —S— atom, or a —$N(R^3)$—, especially —NH— or —$N(CH_3)$—, —C(O)—, —C(S)—, —C(O)O—, —OC(O)—, —$N(R^3)CO$—, especially —NHCO—, or —$CON(R^3)$—, especially —CONH—, group; $Alk^5$ is a $C_{1-6}$ alkylene chain, especially a —$CH_2$—, —$CH_2CH_2$—, —$CH_2CH_2CH_2$— or —$CH_2CH_2CH_2CH_2$— chain; and $R^{10a}$ is a substituted hydroxy group, especially a —$OCH_3$, —$OCH_2CH_3$ or —$OCH(CH_3)_2$ group, a substituted amino group, especially a —$N(CH_3)_2$ or —$N(CH_2CH_3)_2$ group, or a -$Het^2$ group, especially an optionally substituted monocyclic $C_{5-7}$ carbocyclic group containing one, two or three —O—, —S—, —$N(R^{12})$—, especially —NH— or —$N(CH_3)$—, or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group, or $R^{10a}$ is an optionally substituted heteroaromatic group, especially a five- or six-membered monocyclic heteroaromatic group containing one, two, three or four heteroatoms selected from oxygen, sulphur and nitrogen atoms, such as an optionally substituted pyrrolyl, furyl, thienyl, imidazolyl, triazolyl, pyridinyl, pyrimidinyl, triazinyl, pyridazinyl or pyrazinyl group. Particularly preferred optional substituents on the -$Het^2$ groups just described include hydroxy (—OH) and carboxy (—$CO_2H$) groups or those preferred optional substituents just described in relation to the group $Cy^1$.

In one particularly preferred group of compounds of formula (1) $Cy^1$ is an optionally substituted phenyl group, especially a phenyl group optionally substituted by one, two or three optional substituents where at least one, and preferably two, optional substituents are located ortho to the bond joining $Cy^1$ to the remainder of the compound of formula (1). Particularly preferred ortho substituents include halogen atoms, especially fluorine or chlorine atoms, $C_{1-3}$ alkyl groups, especially methyl $C_{1-3}$ alkoxy groups, especially methoxy, halo($C_{1-3}$ alkyl) groups, especially —$CF_3$, halo ($C_{1-3}$ alkoxy) groups, especially —$OCF_3$, and cyano (—CN) groups. In this class of compounds a second or third optional substituent when present in a position other than the ortho positions of the ring $Cy^1$ may be preferably an atom or group —$R^{10a}$ or -$L^6Alk^5(R^{10a})_r$ as herein generally and particularly described.

Particular optional substituents on $Cy^1$ include $C_{1-6}$ alkyl and $C_{1-6}$ alkoxy. Specific optional substituents on $Cy^1$ include methyl and methoxy.

Specific values of $Cy^1$ include phenyl, methylphenyl (especially 4-methylphenyl), methoxyphenyl (especially 4-methoxyphenyl), thienyl (especially thien-3-yl) and indolyl (especially indol-5-yl).

Particularly preferred Ar aromatic groups in compounds of formula (1) include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur and nitrogen atoms. Particularly preferred optionally substituted monocyclic heteroaromatic groups include optionally substituted furyl, thienyl, pyrrolyl, oxazolyl, thiazolyl, pyridinyl, pyrimidinyl or triazinyl groups.

Particularly preferred optional substituents which may be present on Ar aromatic or heteroaromatic groups include atoms or groups —$R^{10a}$ or -$L^6Alk^5(R^{10a})_r$ as hereinbefore defined. Particularly useful optional substituents include halogen atoms, especially fluorine, chlorine or bromine atoms, $C_{1-6}$ alkyl groups, especially $C_{1-3}$ alkyl groups, most especially a methyl group, halo($C_{1-6}$ alkyl) groups, especially fluoro($C_{1-6}$ alkyl) groups, most especially a —$CF_3$ group, $C_{1-6}$ alkoxy groups, especially a methoxy, ethoxy, n-propoxy or isopropoxy group, and halo($C_{1-6}$ alkoxy) groups, especially fluoro($C_{1-6}$ alkoxy) groups, most especially a —$OCF_3$ group, or a cyano (—CN), esterified carboxy, especially —$CO_2CH_3$ or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$, group.

Particularly useful Ar groups in compounds of formula (1) include phenyl and mono- or disubstituted phenyl groups in which each substituent is in particular a —$R^{10a}$ or -$L^6Alk^5(R^{10a})_r$ atom or group as just defined and is especially a halogen atom or a $C_{1-3}$ alkyl, $C_{1-3}$ alkoxy or —CN group.

Suitable values of Ar include phenyl, pyridinyl, thienyl and benzothienyl, any of which groups may be optionally substituted by one or more, typically by one or two, substituents. Examples of typical optional substituents which may be present on Ar include halogen (especially fluoro or chloro), cyano, $C_{1-6}$ alkyl (especially methyl), $C_{1-6}$ alkoxy (especially methoxy) and nitro.

Detailed values of Ar include phenyl, fluorophenyl, difluorophenyl, chlorophenyl, dichlorophenyl, (chloro)(fluoro) phenyl, cyanophenyl, methylphenyl, (fluoro)(methyl)-phenyl, methoxyphenyl, nitrophenyl pyridinyl, chlorothienyl and benzothienyl.

Suitably, $R^{1e}$ represents hydrogen or methyl, especially hydrogen. Suitably, $R^{1f}$ represents hydrogen.

In general, in compounds of formula (1) L is preferably a —$CH_2$— group.

In another embodiment, L is a —$CH(CH_3)$— group.
In a further embodiment, L is a —C(O)— group.
In an additional embodiment, L is a —$CH_2CH_2$— group.

Particularly useful compounds of the invention include each of the compounds described in the Examples hereinafter, and the salts, solvates, hydrates and N-oxides thereof.

Compounds according to the invention, including 3,7-dibenzyl-1,7-dihydro-2H-purinone, are potent and selective inhibitors of p38 kinases, including all isoforms and splice variants thereof. More specifically, the compounds of the invention are inhibitors of p38α, p38β and p38β2. The ability of the compounds to act in this way may be simply determined by employing tests such as those described in the Examples hereinafter.

The compounds of formula (1) and 3,7-dibenzyl-1,7-dihydro-2H-purinone are of use in modulating the activity of p38 kinases and in particular are of use in the prophylaxis and treatment of any p38 kinase mediated diseases or disorders in a human or other mammal. The invention extends to such a use and to the use of the compounds for the manufacture of a medicament for treating such diseases or disorders. Furthermore, the invention extends to the administration to a human of an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production, including for example excessive or unregulated TNF, IL-1, IL-6 and IL-8 production in a human or other mammal. The invention extends to such a use and to the use of the compounds for the manufacture of a medicament for treating such cytokine-mediated diseases or disorders. Furthermore, the invention extends to the administration to a human of an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs host disease and psoriasis.

The invention further extends to the particular autoimmune disease rheumatoid arthritis.

Inflammatory diseases which may be prevented or treated include but are not limited to asthma, allergies, respiratory distress syndrome, and acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastatic melanoma and multiple myeloma.

Neurodegenerative diseases which may be prevented or treated include but are not limited to Parkinson's disease, Alzheimer's disease, cerebral ischemias and neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention exhibit inhibition of expression of inducible pro-inflammatory proteins such as prostaglandin endoperoxidase synthetase-2, otherwise known as cyclooxygenase-2 (COX-2), and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular, these inflammatory mediators have been implicated in pain, such as in the sensitization of pain receptors, or edema. Accordingly, additional p38-mediated conditions which may be prevented or treated include edema, analgesia, fever and pain such as neuromuscular pain, headache, dental pain, arthritis pain and pain caused by cancer.

More particularly, as a result of their p38 inhibitory activity, compounds of the invention have utility in the prevention and treatment of diseases associated with cytokine production including but not limited to those diseases associated with TNF, IL-1, IL-6 and IL-8 production.

Thus, TNF-mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoidosis, bone resorption disease, reperfusion injury, graft vs host reaction, allograft rejections, fever and myalgias due to infection, cachexia secondary to infection, AIDS, ARC or malignancy, keloid formation, scar tissue formation, Crohn's disease, ulcerative colitis, pyresis, and viral infections such as HIV, CMV, influenza and herpes; veterinary viral infections such as lentivirus infections, including but not limited to equine infectious anemia virus, caprine arthritis virus, visna virus or maedi virus; and retrovirus infections, including feline immunodeficiency virus, bovine immunodeficiency virus and canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF-inhibiting compounds of the invention. Such viruses include, but are not limited to, HIV-1, HIV-2 and HIV-3, Cytomegalovirus (CMV), influenza, adenovirus and the herpes group of viruses such as Herpes zoster and Herpes simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al., *Clin. Infec. Dis.*, 1997, 26, 840; Grunberg et al., *Am. J. Crit. Care Med.*, 1997, 155, 1362; Zhu et al., *J. Clin. Invest.*, 1996, 97, 421]. It has also been demonstrated in vitro that infection of pulmonary epithelial cells (which represent the primary site of infection by HRV) with HRV results in production of IL-6 and IL-8 [Sabauste et al., *J. Clin. Invest.*, 1995, 96, 549]. Therefore, p38 inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (1) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 mg/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of the invention may be prepared by a number of processes as generally described below and more specifically in the Examples hereinafter. In the following process description, the symbols Ar, $Cy^1$, $Alk^1$, n, $L^1$, L, $R^a$, A, X and Y when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Greene, T. W. and Wuts, P. G. M., *Protective Groups in Organic Synthesis*, John Wiley and Sons, $3^{rd}$ edition, 1999]. In some instances, deprotection may be the final step in the synthesis of a compound of formula (1) and the processes according to the invention described hereinafter are to be understood to extend to such removal of protecting groups.

Thus, according to a further aspect of the invention, a compound of formula (1) in which $Cy^1$ is as previously defined, but is other than an aromatic or heteroaromatic group when n is zero and $L^1$ is a covalent bond, may be prepared by alkylation of a compound of formula (2):

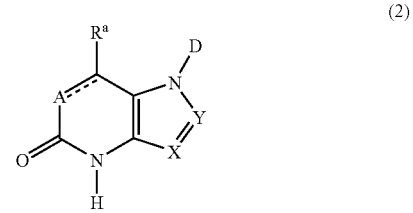

(where D is a hydrogen atom, a group -LAr, or a protecting group), with an alkylating agent of formula $Cy^1L^1(Alk^1)_nZ$, where $Cy^1$ is as just defined and Z is a leaving group such as a halogen atom, e.g. a chlorine, bromine or iodine atom, or a sulphonyloxy group such as an alkylsulphonyloxy, e.g. trifluoromethylsulphonyloxy, or arylsulphonyloxy, e.g. phenylsulphonyloxy, group.

The reaction may be performed in the presence of a solvent, for example a substituted amide such as N,N-dimethylformamide, a cyclic ether such as tetrahydrofuran, a sulphoxide such as dimethylsulphoxide, or mixtures thereof, optionally in the presence of a base, for example an inorganic base such as sodium hydride or potassium carbonate, or an organic base such as an organic amine, e.g. a cyclic amine such as 1,5-diazabicyclo[4.3.0]non-5-ene, or a resin-bound organic amine such as resin-bound 2-tert-butylimino-2-diethylamino-1,3-dimethylperhydro-1,3,2-diazaphosphorine (PS-BEMP), if necessary at an elevated temperature, for example 60 to 100° C.

Intermediates of formula (2) may also be used in another process according to the invention to prepare a compound of formula (1) in which n is zero, $L^1$ is a covalent bond and $Cy^1$ is an optionally substituted aromatic or heteroaromatic group by the reaction of the intermediate with a boronic acid of formula $Cy^1B(OH)_2$ in which $Cy^1$ is as just defined. The reaction may be performed in an organic solvent, for example a halogenated hydrocarbon such as dichloromethane or dichloroethane, in the presence of a copper reagent, for example a copper(II) reagent such as copper(II) acetate, optionally in the presence of an oxidant, for example 2,2,6,6-tetramethyl-1-piperidinyloxy or pyridine N-oxide, optionally in the presence of a base, for example an organic amine such as an alkylamine, e.g. triethylamine, or an aromatic amine, e.g. pyridine, at a temperature from around ambient to the reflux temperature [see for example Chan, D. T. et al., *Tetrahedron Lett.*, 1998, 2933; Lam, P. Y. S. et al., *Tetrahedron Lett.*, 2001, 3415].

Moreover, for the preparation of a compound of formula (1) in which n is zero, $L^1$ is a covalent bond and $Cy^1$ is a phenyl moiety substituted in the ortho and/or para positions by one, two or three nitro groups, the intermediate of formula (2) may be reacted with the appropriate fluoro-substituted nitrobenzene derivative. For example, where $Cy^1$ is 2-nitrophenyl, intermediate (2) will be reacted with 2-fluoronitrobenzene. The reaction is conveniently effected at an elevated temperature in the presence of a strong base, e.g. sodium hydride, typically in a dipolar aprotic solvent such as N,N-dimethylformamide.

Intermediates of formula (2) are either known compounds (see, for example, Andresen et al., ibid.) or may be prepared in a multi-step process, firstly by oxidation of the corresponding pyridines or pyrimidines of formula (3):

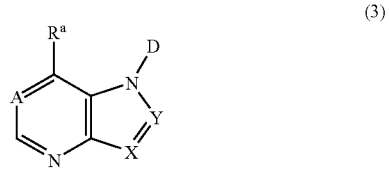

(3)

with an oxidising agent such as hydrogen peroxide in the presence of an acid such as acetic acid, at an elevated temperature, for example around 70° C. to 80° C., or alternatively by reaction with a peracid such as peracetic acid or m-chloroperoxybenzoic acid in a solvent such as an ester, e.g. ethyl acetate, a halogenated hydrocarbon, e.g. dichloromethane, or an alcohol, e.g. tert-butanol, at a temperature from the ambient temperature to the reflux temperature, to yield the corresponding N-oxide; followed by sequential reaction with an anhydride, for example acetic anhydride, at an elevated temperature, such as the reflux temperature, and then with an inorganic base, for example a carbonate such as aqueous potassium carbonate, in a solvent such as an ether, for example a cyclic ether, e.g. tetrahydrofuran, at around ambient temperature, to yield the desired intermediate of formula (2). Alternatively the N-oxide may be treated with trifluoroacetic anhydride in N,N-dimethylformamide from 0° C. to ambient temperature to yield the desired intermediate [see, for example, Konno et al., *Heterocycles*, 1986, 24, 2169].

Intermediates of formula (3) in which D is a protecting group can be advantageously used in the above reactions to generate a variety of compounds of the invention. Thus, for example, an intermediate of formula (3) in which D is a phenylsulphonyl group may be oxidised, converted to the corresponding pyridinone or pyrimidinone of formula (2), and then alkylated or arylated according to the reactions described above. At this point the phenylsulphonyl group can be removed, for example by treatment with a base such as sodium hydroxide in an alcohol such as methanol at ambient temperature. The resulting deprotected intermediate can then be reacted, in another process according to the invention, with a compound ArLZ (where Z is a leaving group as defined above) in the presence of a base and suitable solvent, as described above for the alkylation of intermediates of formula (2), to yield a desired compound of formula (1).

Where in the general processes described above intermediates of formula (3), other intermediates such as alkylating agents of formula $Cy^1L^1(Alk^1)_nZ$, and any other intermediates required in the synthesis of compounds of the invention, are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds.

Thus, for example, intermediates of formula (3) where D is a protecting group such as an arylsulphonyl group may be obtained from the corresponding 1H-compounds by reaction with a compound $ArSO_2Hal$ (where Hal is a halogen atom such as a chlorine atom) in the presence of a base such as sodium hydride in a solvent such as dimethylsulphoxide at ambient temperature. Similarly, compounds of the invention and intermediates thereto generally may be obtained by sulphonylation of a compound containing an —OH group by reaction with one of the above alkylating agents but in which Z is replaced by a —S(O)Hal or —$SO_2$Hal group in the presence of a base, for example an inorganic base such as sodium hydride, in a solvent such as an amide, e.g. a substituted amide such as N,N-dimethylformamide, at, for example, ambient temperature.

Compounds of the invention and intermediates thereto where A represents a —N($R^b$)— or —C($R^b$)($R^c$)— group may be generated from corresponding compounds of the invention or intermediates thereto where A represents a —N= or —C($R^b$)= group by reduction, for instance by catalytic hydrogenation using a metal catalyst such as palladium on charcoal in the presence of hydrogen gas at an elevated pressure in a solvent such as an alcohol, e.g. ethanol, optionally at an elevated temperature, e.g. between 40° C. and 60° C.

Aromatic halogen substituents in the compounds of the invention may be subjected to halogen-metal exchange with a base, for example a lithium base such as n-butyllithium or tert-butyllithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile, a thiomethyl group may be introduced by using dimethyldisulphide as the electrophile, an alcohol group may be introduced by using an aldehyde as the electrophile, and an acid may be introduced by using carbon dioxide as the electrophile. Aromatic acids of formula $ArCO_2H$ may also be generated by quenching Grignard reagents of formula ArMgHal with carbon dioxide.

Aromatic acids of formula $ArCO_2H$ generated by this method and acid-containing compounds in general may be converted to activated derivatives, e.g. acid halides, by reaction with a halogenating agent such as a thionyl halide, e.g. thionyl chloride, a phosphorus trihalide such as phosphorus trichloride, or a phosphorus pentahalide such as phosphorus pentachloride, optionally in an inert solvent such as an aromatic hydrocarbon, e.g. toluene, or a chlorinated hydrocarbon, e.g. dichloromethane, at a temperature from about 0° C. to the reflux temperature, or may be converted into Weinreb amides of formula ArC(O)N(OMe)Me by direct treatment with the amine of formula HN(OMe)Me and a condensing agent such as EDC (vide infra), typically in the presence of a base such as triethylamine in a solvent such as dichloromethane; or by conversion to the acid halide as just described and subsequent reaction with the amine of formula HN(OMe)Me or a salt thereof, optionally in the presence of a base such as an organic amine, e.g. triethylamine, in an inert solvent such as an aromatic hydrocarbon, e.g. toluene, or a chlorinated hydrocarbon, e.g. dichloromethane, at a temperature from about 0° C. to ambient temperature.

Acid (—$CO_2H$) groups in the compounds of the invention or intermediates thereto may be transformed into amide (—$CONH_2$) groups by treatment with ammonia in the presence of a condensing agent, for example 1,1'-carbonyldiimidazole, typically in a solvent such as N,N-dimethylformamide. Similarly, acid (—$CO_2H$) groups in the compounds of the invention or intermediates thereto may be transformed into hydrazide (—$CONHNH_2$) groups by treatment with hydrazine hydrate, suitably in an alcoholic solvent such as 2-ethoxyethanol, typically at an elevated temperature.

Amide (—$CONH_2$) groups in the compounds of the invention or intermediates thereto may be transformed into cyano (—CN) groups by treatment with trifluoroacetic anhydride in the presence of pyridine and a solvent, e.g. a chlorinated solvent such as dichloromethane.

Compounds of formula (1) wherein $R^e$ represents —$CO_2H$ may be converted into the corresponding compound wherein $R^e$ represents —$CONR^{1a}R^{2a}$ by conversion into an activated derivative, e.g. an acid halide, as described above, typically in a dipolar aprotic solvent such as N,N-dimethylformamide; followed by treatment with the appropriate amine of formula H—$NR^{1a}R^{2e}$, typically in an inert solvent such as tetrahydrofuran Alternatively, a compound of formula (1) wherein $R^e$ represents —$CO_2H$ may be converted directly into the corresponding compound wherein $R^e$ represents —$CONR^{1a}R^{2a}$ by treatment with the appropriate amine of formula H—$NR^{1a}R^{2a}$ and a condensing agent such as EDC (vide infra), suitably in the presence of a catalyst such as 1-hydroxybenzotriazole, typically in an inert solvent, e.g. a chlorinated solvent such as dichloromethane.

Compounds of the invention and intermediates thereto may be prepared by alkylation, arylation or heteroarylation. For example, compounds containing a -$L^1H$ group (where $L^1$ is a linker atom or group) may be treated with an alkylating agent $Cy^1Z^2$ in which $Z^2$ is a leaving atom or group such as a halogen atom, e.g. a fluorine, chlorine, bromine or iodine atom, or a sulphonyloxy group such as an alkylsulphonyloxy, e.g. trifluoromethylsulphonyloxy, or arylsulphonyloxy, e.g. p-toluenesulphonyloxy, group.

The reaction may be carried out in the presence of a base such as a carbonate, e.g. caesium carbonate or potassium carbonate, an alkoxide, e.g. potassium tert-butoxide, or a hydride, e.g. sodium hydride, in a dipolar aprotic solvent such as an amide, e.g. a substituted amide such as N,N-dimethylformamide, or an ether, e.g. a cyclic ether such as tetrahydrofuran.

In another example, compounds containing a -$L^2H$ group as defined above may be functionalised by acylation or thioacylation, for example by reaction with the alkylating agents just described but in which $Z^2$ is replaced by a —$C(O)Z^3$, —$C(S)Z^3$, —$N(R^2)C(O)Z^3$ or —$N(R^2)C(S)Z^3$ group in which $Z^3$ is a leaving atom or group as described for $Z^2$. The reaction may be performed in the presence of a base, such as a hydride, e.g. sodium hydride, or an amine, e.g. triethylamine or N-methylmorpholine, in a solvent such as a halogenated hydrocarbon, e.g. dichloromethane or carbon tetrachloride, or an amide, e.g. N,N-dimethylformamide, at for example ambient temperature. Alternatively, the acylation may be carried out under the same conditions with an acid (for example one of the alkylating agents described above in which $Z^2$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, or a benzotriazole such as O-(7-azabenzotriazol-1-yl)-N,N,N,N-tetramethyluronium hexafluorophosphate, advantageously in the presence of a catalyst such as a N-hydroxy compound, e.g. a N-hydroxytriazole such as 1-hydroxybenzotriazole. Alternatively, the acid may be reacted with a chloroformate, for example ethyl chloroformate, prior to the desired acylation reaction.

In another example, compounds containing a -$L^2H$ group as defined above may be coupled with one of the alkylation agents just described but in which $Z^2$ is replaced by an —OH group in a solvent such as tetrahydrofuran in the presence of a phosphine, e.g. triphenylphosphine, and an activator such as diethyl, diisopropyl or dimethyl azodicarboxylate.

Ester groups such as —$CO_2Alk^6$, —$CO_2R^4$ and —$CO_2R^1$ (where $R^1$ is other than hydrogen) in the compounds of formula (1) and intermediates thereto may be converted to the corresponding acid (—$CO_2M$) by acid- or base-catalysed hydrolysis depending on the nature of the group $Alk^6$, $R^4$ or $R^1$. Acid- or base-catalysed hydrolysis may be achieved, for example, by treatment with an organic or inorganic acid, e.g. trifluoroacetic acid, in an organic solvent, e.g. dichloromethane, or a mineral acid such as hydrochloric acid in a solvent such as 1,4-dioxane, or an alkali metal hydroxide, e.g. lithium hydroxide or sodium hydroxide, in an aqueous alcohol, e.g. aqueous methanol or aqueous ethanol.

In a further example, —$OR^6$ (where $R^6$ represents an alkyl group such as methyl) in compounds of formula (1) and intermediates thereto may be cleaved to the corresponding alcohol —OH by reaction with boron tribromide in a solvent such as a halogenated hydrocarbon, e.g. dichloromethane, at a low temperature, e.g. around −78° C.

Alcohol (—OH) groups may also be obtained by hydrogenation of a corresponding —$OCH_2R^{31}$ group (where $R^{31}$ is an aryl group) using a metal catalyst, for example palladium on a support such as carbon, in a solvent such as ethanol in the presence of ammonium formate, cyclohexadiene or hydrogen, from around ambient temperature to the reflux temperature. In another example, —OH groups may be generated from the corresponding ester (e.g. —$CO_2Alk^6$) or aldehyde (—CHO) by reduction, using for example a complex metal hydride such as lithium aluminium hydride or sodium borohydride in a solvent such as methanol.

In another example, —OH groups in the compounds may be converted to a corresponding —$OR^6$ group by coupling with a reagent $R^6OH$ in a solvent such as tetrahydrofuran in the presence of a phosphine, e.g. triphenylphosphine and an activator such as diethyl, diisopropyl or dimethyl azodicarboxylate.

Aminosulphonylamino (—$NHSO_2NH_2$) groups in the compounds may be obtained, in another example, by reaction of a corresponding amine (—$NH_2$) with sulphamide in the presence of an organic base such as pyridine at an elevated temperature, e.g. the reflux temperature.

In another example, compounds containing a —$NHCSR^7$ or —$CSNHR^7$ group may be prepared by treating a corresponding compound containing a —$NHCOR^7$ or —$CONHR^7$ group with a thiation reagent, such as Lawesson's Reagent or $P_2S_5$, in an anhydrous solvent, for example a cyclic ether such as tetrahydrofuran, at an elevated temperature such as the reflux temperature.

In a further example, amine (—NH$_2$) groups may be alkylated using a reductive alkylation process employing an aldehyde and a reducing agent. Suitable reducing agents include borohydrides, for example sodium triacetoxyborohydride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon, e.g. toluene, and then subjected to hydrogenation in the presence of a metal catalyst, for example palladium on a support such as carbon, in a solvent such as an alcohol, e.g. ethanol.

Amine (—NH$_2$) groups in the compounds of the invention or intermediates thereto may generally be transformed into halogen atoms, e.g. bromo, by treatment with a nitrite reagent, e.g. tert-butyl nitrite, in the presence of a copper(II) halide, e.g. copper(II) bromide, typically in a solvent such as acetonitrile.

In a further example, amine (—NH$_2$) groups in compounds of formula (1) and intermediates thereto may be obtained by hydrolysis from a corresponding imide by reaction with hydrazine in a solvent such as an alcohol, e.g. ethanol, at ambient temperature.

In another example, a nitro (—NO$_2$) group may be reduced to an amine (—NH$_2$), for example by catalytic hydrogenation using for example hydrogen in the presence of a metal catalyst, for example palladium on a support such as carbon, in a solvent such as an ether, e.g. tetrahydrofuran, or an alcohol, e.g. methanol, or by chemical reduction using for example a metal, e.g. tin or iron, in the presence of an acid such as hydrochloric acid.

In a further example, amine (—CH$_2$NH$_2$) groups in compounds of formula (1) and intermediates thereto may be obtained by reduction of nitriles (—CN), for example by catalytic hydrogenation using for example hydrogen in the presence of a metal catalyst, for example palladium on a support such as carbon, or Raney® nickel, in a solvent such as an ether, e.g. a cyclic ether such as tetrahydrofuran, or an alcohol, e.g. methanol or ethanol, optionally in the presence of ammonia solution at a temperature from ambient temperature to the reflux temperature, or by chemical reduction using for example a metal hydride, e.g. lithium aluminium hydride, in a solvent such as an ether, e.g. a cyclic ether such as tetrahydrofuran, at a temperature from 0° C. to the reflux temperature.

In another example, sulphur atoms in the compounds, for example when present in a group $L^1$ or $L^2$, may be oxidised to the corresponding sulphoxide or sulphone using an oxidising agent such as a peroxyacid, e.g. 3-chloroperoxybenzoic acid, in an inert solvent such as a halogenated hydrocarbon, e.g. dichloromethane, at around ambient temperature.

In a further example, N-oxides of compounds of formula (1) may in general be prepared for example by oxidation of the corresponding nitrogen base as described above in relation to the preparation of intermediates of formula (2).

Salts of compounds of formula (1) may be prepared by reaction of compounds of formula (1) with an appropriate base in a suitable solvent or mixture of solvents, e.g. an organic solvent such as an ether, e.g. diethyl ether, or an alcohol, e.g. ethanol, using conventional procedures.

Where it is desired to obtain a particular enantiomer of a compound of formula (1) this may be produced from a corresponding mixture of enantiomers using any suitable conventional procedure for resolving enantiomers.

Thus, for example, diastereomeric derivatives, e.g. salts, may be produced by reaction of a mixture of enantiomers of formula (1), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt.

In another resolution process a racemate of formula (1) may be separated using chiral High Performance Liquid Chromatography. Alternatively, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

EtOAc—ethyl acetate;
DCM—dichloromethane;
DMSO—dimethylsulphoxide;
THF—tetrahydrofuran;
MCPBA—3-chloroperoxybenzoic acid;
r.t.—room temperature;
AcOH—acetic acid;
UHP—urea-hydrogen peroxide complex;
TLC—thin-layer chromatography;
MeOH—methanol;
EtOH—ethanol; Pyr—pyridine;
Me—methyl;
h—hour;
DMF—N,N-dimethylformamide;
TFAA—trifluoroacetic anhydride;
CDI—1,1'-carbonyldiimidazole;
EDC—1-[3-(dimethylamino)propyl]-3-ethylcarbodiimide hydrochloride;
HOBT—1-hydroxybenzotriazole hydrate.

All NMRs were obtained either at 300 MHz or 400 MHz.

Compounds were named with the aid of either Beilstein Autonom, supplied by MDL Information Systems GmbH, Theodor-Heuss-Allee 108, D-60486 Frankfurt, Germany, or ACD Labs Name (v. 5.0 or v. 6.0), supplied by Advanced Chemical Development, Toronto, Canada. LCMS retention times (RT) quoted were generated on a Hewlett Packard 1100 LC/MS using the following method unless otherwise stated: Phenomenex Luna 3μ C$_{18}$(2) 50×4.6 mm column; mobile phase A=0.1% formic acid in water, mobile phase B=0.1% formic acid in MeCN; flow rate of 0.9 mlmin$^{-1}$; column temperature 40° C.

Gradient:

| Time (min) | % B |
| --- | --- |
| Initial | 5 |
| 2.0 | 95 |
| 3.0 | 95 |
| 5.0 | 5 |
| 5.5 | end |

LCMS Method B: Phenomenex Luna 3μ C$_{18}$(2) 50×4.6 mm column; mobile phase A=0.1% formic acid in water; mobile phase B=0.1% formic acid in MeCN; flow rate of 0.9 mlmin$^{-1}$; column temperature 40° C.

Gradient:

| Time (min) | % B |
|---|---|
| Initial | 5 |
| 2.0 | 95 |
| 4.0 | 95 |
| 5.0 | 5 |
| 5.5 | end |

LCMS Method C: Varian Polaris 5μ $C_{18}$ 50×4.6 mm column; mobile phase A=0.1% formic acid in water; mobile phase B=0.1% formic acid in MeCN; flow rate of 0.9 mlmin$^{-1}$; column temperature 40° C.

Gradient:

| Time (min) | % B |
|---|---|
| Initial | 5 |
| 1.0 | 95 |
| 5.0 | 95 |
| 5.5 | end |

Intermediate 1

1-Benzenesulfonyl-1H-pyrrolo[3,2-b]pyridine

Sodium hydride (60% in mineral oil, 203 mg, 5.08 mmol) was washed twice with hexane, and the residue suspended in DMSO (5 ml). 1H-Pyrrolo[3,2-b]pyridine (500 mg, 4.24 mmol) was added and the reaction stirred for 15 minutes. Benzenesulphonyl chloride (749 mg, 4.42 mmol) was added rapidly and the reaction stirred for 0.5 h. After quenching with water the product was extracted into EtOAc, dried ($Na_2SO_4$) and concentrated in vacuo. Chromatography (EtOAc, silica) yielded the title compound as a white crystalline solid (903 mg, 83%). $\delta_H$ ($d_6$-DMSO) 8.48 (1H, dd, J 0.8, 3.8 Hz), 8.31 (1H, m), 8.15 (1H, d, J 3.8 Hz), 8.04 (2H, m), 7.72 (1H, m,), 7.61 (2H, m,), 7.36 (1H, dd, J 4.7, 8.4 Hz), 6.98 (1H, dd, J 0.8, 3.8 Hz). LCMS (ES$^+$) RT 3.056 minutes, 259 (M+H)$^+$.

Intermediate 2

1-Benzenesulfonyl-1H-pyrrolo[3,2-b]pyridine 4-oxide

Intermediate 1 (903 mg, 3.5 mmol) was dissolved in EtOAc (6 ml) and treated with MCPBA (903 mg, 5.25 mmol). After stirring for 24 h the reaction mixture was washed with saturated sodium hydrogencarbonate solution, dried ($MgSO_4$) and concentrated in vacuo. Chromatography (EtOAc, silica) yielded the title compound as a white foam (860 mg, 90%). $\delta_H$ ($d_6$-DMSO) 8.24 (1H, d, J 6.6 Hz), 8.15 (3H, m), 7.9 (1H, d, J 8.3 Hz), 7.76 (1H, m), 7.68 (2H, m), 7.35 (1H, dd, J 6.3, 8.5 Hz), 7.1 (1H, dd, J 0.8, 3.8 Hz). LCMS (ES$^+$) RT 2.639 minutes, 275 (M+H$^+$).

Intermediate 3

1-Benzenesulfonyl-1,4-dihydro-5H-pyrrolo[3,2-b]pyridin-5-one

Intermediate 2 (0.86 g, 3.1 mmol) was dissolved in DMF (8 ml) and treated with TFAA (6.6 g, 31.4 mmol) at r.t. and stirred for 4 days. The reaction mixture was concentrated in vacuo, redissolved in EtOH, concentrated again, then partitioned between water and toluene. The organic layer was dried ($MgSO_4$) and concentrated to yield the title compound as a beige solid (657 mg, 77%). $\delta_H$ ($d_6$-DMSO) 8.20 (1H, d, J 8.6 Hz), 8.11 (2H, m), 7.94 (1H, d, J 3.7 Hz), 7.88 (1H, d, J 8.4 Hz), 7.78 (2H, m), 6.58 (1H, d, J 3.6 Hz), 6.45 (1H, d, J 9.6 Hz). LCMS (ES$^+$) RT 2.775 minutes, 275 (M+H)$^+$.

Intermediate 4

1-Benzenesulfonyl-4-phenyl-1,4-dihydro-5H-pyrrolo[3,2-b]pyridin-5-one

Intermediate 3 (300 mg, 1.09 mmol) was combined with phenylboronic acid (343 mg, 2.19 mmol), copper(II) acetate (437 mg, 2.19 mmol), and pyridine (319 mg, 0.41 ml, 3.28 mmol) in DCM. The reaction was stirred at r.t. for 24 h then diluted with further DCM, washed with water, and the organic layer dried and concentrated in vacuo. Column chromatography (EtOAc, silica) yielded the title compound (150 mg, 39%). $\delta_H$ ($d_6$-DMSO) 7.95 (1H, d, J 9.8 Hz), 7.90 (2H, d, J 8.5 Hz), 7.60 (2H, m), 7.53 (2H, m), 7.35 (3H, m), 7.16 (2H, d, J 1.7, 8.3 Hz), 6.23 (1H, d, J 9.8 Hz), 5.70 (1H, dd, J 0.6, 3.7 Hz). LCMS (ES$^+$) RT 3.312 minutes, 351 (M+H)$^+$.

Intermediate 5

4-Phenyl-1,4-dihydro-5H-pyrrolo[3,2-b]pyridin-5-one

Intermediate 4 (1.5 g, 4.3 mmol) in MeOH (10 ml) was treated with 2M sodium hydroxide (5 ml) and stirred at r.t. for 2 h. The organic phase was removed under reduced pressure, the residue neutralised with 2M hydrochloric acid then extracted into DCM, dried ($MgSO_4$) and concentrated in vacuo to yield the title compound (765 mg, 85%). $\delta_H$ ($CDCl_3$) 9.30 (1H, br s), 7.44 (3H, m), 7.36 (3H, m), 6.84 (1H, t, J 3.0 Hz), 6.37 (1H, d, J 9.4 Hz), 5.59 (1H, t, J 2.3 Hz).

Intermediate 6

1-Benzenesulfonyl-4-(4-methoxyphenyl)-1,4-dihydro-5H-pyrrolo[3,2-b]pyridin-5-one From Intermediate 3 (300 mg, 1.09 mmol) and 4-methoxyphenylboronic acid (333 mg, 2.19 mmol) by the method of Intermediate 4 to give the title compound (110 mg, 27%). $\delta_H$ ($d_6$-DMSO) 8.12 (1H, d, J 9.8 Hz), 8.06 (2H, m), 7.75 (4×, m), 7.25 (2H, dd, J 2.2, 9.0 Hz), 7.05 (2H, dd, J 2.2, 9.0 Hz), 6.40 (1H, d, J 9.8 Hz), 5.91 (1H, dd, J 0.5, 3.6 Hz), 3.81 (3H, s). LCMS (ES$^+$) RT 3.309 minutes, 381 (M+H)$^+$.

Intermediate 7

4-(4-Methoxyphenyl)-1,4-dihydro-5H-pyrrolo[3,2-b]pyridin-5-one

From Intermediate 6 (25 mg, 0.066 mmol) by the method of Intermediate 5 to give the title compound (16 mg, 100%). $\delta_H$ ($CDCl_3$) 9.04 (1H, br s), 7.46 (1H, dd, J 0.5, 9.3 Hz), 7.25 (2H, m), 6.96 (2H, m), 6.89 (1H, apparent t, J 2.9 Hz), 6.38 (1H, d, J 9.3 Hz), 5.63 (1H, apparent t, J 2.3 Hz), 3.78 (3H, s). HPLC RT 2.608 minutes.

Intermediate 8

(Phenyl(pyrrolo[3,2-b]pyridin-1-yl)methanone

By the method of Intermediate 1 using benzoyl chloride (596 mg, 4.42 mmol) in place of benzenesulphonyl chloride. Yellow crystalline solid (429 mg, 44%). $\delta_H$ (d$_6$-DMSO) 8.60 (1H, m), 8.50 (1H, m), 7.79 (2H, m), 7.74 (2H, m), 7.63 (2H, m), 7.39 (1H, dd, J 4.7, 8.3 Hz), 6.86 (1H, dd, J 0.6, 3.9 Hz). LCMS (ES$^+$) RT 2.622 minutes, 223 (M+H)$^+$.

Intermediate 9

(4-Oxypyrrolo[3,2-b]pyridin-1-yl)(phenyl)methanone

From Intermediate 8 (429 mg, 1.93 mmol) by the method of Intermediate 2. White foam (403 mg, 88%). $\delta_H$ (d$_6$-DMSO) 8.28 (1H, d, J 7.7 Hz), 8.10 (1H, d, J 8.8 Hz), 7.81 (2H, d, J 7.7 Hz), 7.74 (1H, m), 7.67 (3H, m), 7.38 (1H, dd, J 6.4, 8.5 Hz), 6.98 (1H, m). LCMS (ES$^+$) RT 2.612 minutes, 239 (M+H)$^+$.

Intermediate 10

1-Benzoyl-1,4-dihydro-5H-pyrrolo[3,2-b]pyridin-5-one

Intermediate 9 (400 mg, 1.68 mmol) was dissolved in DMF (4 ml) and treated dropwise with TFAA (3.5 g, 16.8 mmol) then stirred at r.t. for 4 days. The reaction mixture was concentrated in vacuo, redissolved in ethanol, concentrated again, and finally azeotroped with heptane to remove the remaining TFAA. The residue was partitioned between toluene and water, and the organic phase separated, dried (Na$_2$SO$_4$) and concentrated in vacuo to give the title compound as a white crystalline solid (218 mg, 55%). $\delta_H$ (d$_6$-DMSO) 8.18 (1H, d, J 9.6 Hz), 7.78-7.64 (3H, m), 7.64-7.51 (2H, m), 7.31 (1H, d, J 3.5 Hz), 6.30 (1H, m), 6.25 (1H, d, J 9.7 Hz). HPLC RT 2.717 minutes.

Intermediate 11

4-Phenyl-1-(phenylsulfonyl)-2-(pyrolidin-1-ylsulfonyl)-1,4-dihydro-5H-pyrrolo[3,2-b]pyridin-5-one A solution of Intermediate 4 (400 mg, 1.14 mmol) in THF (6 ml) was cooled to −78° C. under nitrogen and treated dropwise with n-BuLi (1.6 M in hexanes, 0.86 ml, 1.37 mmol) and stirred for 30 minutes. Sulphur dioxide was blown through the reaction mixture at −78° C. for 5 minutes and the reaction mixture was then allowed to warm to r.t. The solvents were removed in vacuo and the residue suspended in DCM (10 ml). N-Chlorosuccimide (203 mg, 1.14 mmol) was added and the reaction stirred for 30 minutes, then treated with pyrrolidine (81 mg, 0.095 ml, 1.14 mmol). After stirring for a further 30 minutes the reaction was partitioned between water and DCM, and the organic phase was dried (Na$_2$SO$_4$), concentrated and purified by chromatography (EtOAc, silica) to give the title compound (210 mg, 38%). LCMS Method B (ES$^+$) RT 2.410 minutes, 484 (M+H$^+$).

Intermediate 12

4-Phenyl-2-(pyrolidin-1-ylsulfonyl)-1,4-dihydro-5H-pyrrolo[3,2-b]-5-one

Intermediate 11 (200 mg, 0.41 mmol) was suspended in 2M sodium hydroxide (10 ml) and treated with sufficient MeOH to solubilise. The reaction was stirred at r.t. for 3 days. The MeOH was removed in vacuo and the residual aqueous solution washed with DCM. After acidification with conc. HCl the product was extracted into DCM, and the organic phase dried (Na$_2$SO$_4$) and concentrated in vacuo. Purification of the residue by chromatography (EtOAc, silica) gave the title compound (140 mg, 100%). $\delta_H$ (d$_6$-DMSO) 7.76 (1H, d, J 9.6 Hz), 7.67-7.61 (2H, m), 7.58-7.55 (1H, m), 7.48-7.45 (2H, m), 6.51 (1H, d, J 9.6 Hz), 5.97 (1H, s), 3.22-3.17 (4H, m), 1.74-1.69 (4H, m). LCMS (ES$^+$) RT 2.801 minutes, 344 (M+H$^+$).

Intermediate 13

Ethyl (2Z)-2-hydroxy-3-(3-nitropyridin-2-yl)acetate

Sodium metal (400 ng, 17.4 mmol) was added portionwise to EtOH (50 ml), followed by diethyl oxalate (2.4 ml, 17.4 mmol), and stirred at r.t. for 5 mill 2-Methyl-3-nitropyridine (2.00 g, 14.6 mmol) was added, giving a deep purple solution that changed over time to red-orange. After stirring for 3 days at r.t. a red precipitate had formed which was collected by filtration and washed with ether (4×20 ml). The solid residue was suspended in water and the suspension acidified to pH 4 with AcOH. The resulting orange precipitate was collected by filtration, washed with ethanol (10 ml) and dried in vacuo to give the title compound (1.17 g, 34%). $\delta_H$ (CDCl$_3$) 8.77-8.75 (1H, m), 8.54-8.50 (1H, m), 7.47-7.43 (2H, m), 4.48 (2H, q, J 7.1 Hz), 1.49 (3H, t, J 7.1 Hz). LCMS (ES$^+$) RT 3.32 minutes, 239 (M+H$^+$).

Intermediate 14

Ethyl 1H-pyrrolo[3,2-b]pyridine-2-carboxylate

A mixture of Intermediate 13 (6.30 g, 26.5 mmol) and iron powder (325 mesh, 13.3 g, 238.2 mmol) in EtOH (100 ml) and AcOH (100 ml) was heated at reflux for 2 h. Volatiles were removed in vacuo and toluene used to azeotrope excess AcOH (3×100 ml). The brown residue was suspended in EtOAc and passed through a plug of silica gel, eluting the desired product with EtOAc. Concentration of the eluent in vacuo gave the title compound as an off-white solid (4.32 g, 86%). $\delta_H$ (d$_3$-MeOD) 8.33-8.30 (1H, m), 7.84-7.80 (1H, m), 7.22 (1H, dd, J 4.6, 8.4 Hz), 7.14 (1H, d, J 0.9 Hz), 4.33 (2H, q, J 7.1 Hz), 1.33 (3H, t, J 7.1 Hz). LCMS Method C (ES$^+$) RT 1.22 minutes, 191 (M+H$^+$).

Intermediate 15

Ethyl 1-benzyl-1H-pyrrolo[3,2-b]pyridine-2-carboxylate

A solution of Intermediate 14 (200 mg, 1.05 mmol) in DMF (10 ml) was treated with sodium hydride (60% in mineral oil, 42 mg, 1.05 mmol) at r.t. until effervescence ceased. After cooling to 0° C., benzyl bromide (0.13 ml, 1.05 mmol) was added and the reaction stirred for 10 minutes. The reaction mixture was partitioned between water and EtOAc (20 ml each) and extracted with EtOAc (20 ml). The combined organics were washed with brine (20 ml), dried (MgSO$_4$), filtered and concentrated in vacuo. Purification by chromatography (5%-20% MeOH in DCM, silica) gave the title compound as a yellow solid (143 mg, 48%). $\delta_H$ (CDCl$_3$) 8.38-8.36 (1H, m), 7.50-7.46 (1H, m), 7.36 (1H, s), 7.20-7.01 (4H, m), 6.88-6.85 (2H, m), 5.69 (2H, s), 4.20 (2H, q, J 7.1 Hz), 1.21 (3H, t, J 7.1 Hz). LCMS (ES$^+$) RT 3.16 minutes, 281 (M+H$^+$).

Intermediate 16

Ethyl 1-benzyl-1H-pyrrolo[3,2-b]pyridine-2-carboxylate 4-oxide

A solution of Intermediate 15 (140 mg, 0.5 mmol) in THF (1 ml) at 0° C. was treated with UHP (99 mg, 1.05 mmol). Slow addition of TFAA (0.15 ml, 1.05 mmol) was followed by stirring at 0° C. for 30 min. The reaction mixture was treated with dilute aqueous sodium thiosulfate solution (5 ml) for 30 min then acidified with dilute HCl. Extraction with DCM (2×5 ml), drying (MgSO$_4$), filtration and concentration in vacuo, then purification by chromatography (50% EtOAc in DCM-15% MeOH in EtOAc, silica) gave the title compound as a yellow solid (120 mg, 81%). $\delta_H$ (CDCl$_3$) 8.14 (1H, d, J 8.5 Hz), 7.68 (1H, s), 7.15-7.12 (4H, m), 7.08-6.95 (3H, m), 5.79 (2H, s), 4.29 (2H, q, J 7.1 Hz), 1.30 (3H, t, J 7.1 Hz). LCMS Method C (ES$^+$) RT 2.33 minutes, 297 (M+H$^+$).

Intermediate 17

Ethyl 1-benzyl-5-oxo-4,5-dihydro-1H-pyrrolo[3,2-b]pyridine-2-carboxylate

A solution of Intermediate 16 (120 mg, 0.40 mmol) in DMF (1 ml) was treated with TFAA (0.57 ml, 4.05 mmol) and stirred at r.t. for 2 h. The reaction mixture was partitioned between EtOAc and NaHCO$_3$ (20 ml each) and the organics washed with water (5 ml), then brine (5 ml), dried (MgSO$_4$), filtered and concentrated in vacuo to give the title compound. $\delta_H$ (CDCl$_3$) 7.47 (1H, d, J 9.6 Hz), 7.16-7.25 (3H, m), 6.97-6.95 (3H, m), 6.46 (1H, d, J 9.6 Hz), 5.71 (2H, s), 4.22 (2H, q, J 7.1 Hz), 1.26 (3H, t, J 7.1 Hz). LCMS Method C (ES$^+$) RT 2.25 minutes, 297 (M+H$^+$).

Intermediate 18

Ethyl 1-(3-chloro-4-fluorobenzyl)-1H-pyrrolo[3,2-b]pyridine-2-carboxylate

From Intermediate 14 (1.00 g, 5.26 mmol) and 3-chloro-4-fluorobenzyl bromide (1.30 g, 5.80 mmol) by the method of Intermediate 15. Purification by chromatography (20%-50% EtOAc in hexane, silica) gave the title compound (1.09 g, 62%). $\delta_H$ (CDCl$_3$) 8.64-8.63 (1H, m), 7.67 (1H, d, J 9.6 Hz), 7.57 (1H, s), 7.29-7.25 (1H, m), 7.16-7.04 (2H, m), 6.95-6.90 (1H, m), 5.81 (2H, s), 4.42 (2H, q, J 7.1 Hz), 1.43 (3H, t, J 7.1 Hz). LCMS (ES$^+$) RT 3.36 minutes, 333 [$^{35}$Cl]:335 [$^{37}$Cl] 3:1 (M+H$^+$).

Intermediate 19

Ethyl 1-(3-chloro-4-fluorobenzyl)-1H-pyrrolo[3,2-b]pyridine-2-carboxylate 4-oxide From Intermediate 18 (1.09 g, 3.28 mmol), with UHP (650 mg, 6.89 mmol) and TFAA (0.97 ml, 6.89 mmol) by the method of Intermediate 16. Purification by chromatography (5%-15% MeOH in EtOAc, silica) gave the title compound (920 mg, 81%). $\delta_H$ (CDCl$_3$) 8.14-8.11 (1H, m), 7.68 (1H, s), 7.18-7.14 (1H, m), 7.04-6.90 (3H, m), 6.81-6.76 (1H, m), 5.65 (2H, s), 4.24 (2H, q, J 7.1 Hz), 1.26 (3H, t, J 7.1 Hz). LCMS Method C(ES$^+$) RT 2.39 minutes, 349 [$^{35}$Cl]:351 [$^{37}$Cl] 3:1 (M+H$^+$).

Intermediate 20

Ethyl 1-(3-chloro-4-fluorobenzyl)-5-oxo-4,5-dihydro-1H-pyrrolo[3,2-b]pyridine-2-carboxylate From Intermediate 19 (910 mg, 2.61 mmol) and TFAA (3.70 ml, 26.1 mmol) by the method of Intermediate 17. The compound required no further purification (886 mg, 97%). $\delta_H$ (CDCl$_3$) 7.84 (1H, d, J 9.6 Hz), 7.11-6.68 (3H, m), 6.82 (1H, s), 6.42 (1H, d, J 9.6 Hz), 5.69 (2H, s), 4.23 (2H, q, J 7.1 Hz), 1.23 (3H, t, J 7.1 Hz). LCMS (ES$^+$) RT 3.22 minutes, 349 [$^{35}$Cl]:351 [$^{37}$Cl] 3:1 (M+H$^+$).

Intermediate 21

Ethyl 1-(3-methylbenzyl)-1H-pyrrolo[3,2-b]pyridine-2-carboxylate

From Intermediate 14 (1.00 g, 5.26 mmol) and 3-methylbenzyl bromide (0.78 ml, 5.80 mmol) according to the procedure for Intermediate 15. Purification by chromatography (50% EtOAc in hexane, silica) gave the title compound (520 mg, 34%). $\delta_H$ (CDCl$_3$) 8.38-8.36 (1H, m), 7.45 (1H, d, J 9.6 Hz), 7.32 (1H, s), 7.03-6.82 (3H, m), 6.72-6.60 (2H, m), 5.63 (2H, s), 4.18 (2H, q, J 7.1 Hz), 2.07 (3H, s), 1.19 (3H, t, J 7.1 Hz). LCMS (ES$^+$) RT 3.16 minutes, 294 (M+H$^+$).

Intermediate 22

Ethyl 1-(3-methylbenzyl)-1H-pyrrolo[3,2-b]pyridine-2-carboxylate 4-oxide

From Intermediate 21 (520 mg, 1.77 mmol), using UHP (350 mg, 3.71 mmol) and TFAA (0.53 ml, 3.71 mmol) according to the procedure for Intermediate 16. Purification by chromatography (2%-15% MeOH in EtOAc, silica) gave the title compound (455 mg, 83%). $\delta_H$ (CDCl$_3$) 8.18-8.14 (1H, m), 7.73 (1H, s), 7.28-7.21 (1H, m), 7.14-6.98 (3H, m), 6.76-6.73 (2H, m), 5.75 (2H, s), 4.29 (2H q, J 7.1 Hz), 2.20 (3H, s), 1.31 (3H, t, J 7.1 Hz). LCMS (ES$^+$) RT 2.36 minutes, 311 (M+H$^+$).

Intermediate 23

Ethyl 1-(3-methylbenzyl)-5-oxo-4,5-dihydro-1H-pyrrolo[3,2-b]pyridine-2-carboxylate From Intermediate 22 (450 mg, 1.45 mmol) using TFAA (2.05 ml, 14.5 mmol) according to the procedure for Intermediate 17. Title compound required no further purification (354 mg, 79%). $\delta_H$ (CDCl$_3$) 7.80 (1H, d J 9.6 Hz), 7.12-7.09 (1H, m), 7.03-7.00 (1H, m), 6.84 (2H, s), 6.78-6.76 (1H, m), 6.41 (1H, d, J 9.6 Hz), 5.76 (2H, s), 4.29 (2H, q, J 7.1 Hz), 2.23 (3H, s), 1.29 (3H, t, J 7.1 Hz). LCMS (ES$^+$) RT 3.14 minutes, 311 (M+H$^+$).

Intermediate 24

Ethyl 1-(3-chlorobenzyl)-1H-pyrrolo[3,2-b]pyridine-2-carboxylate

From Intermediate 14 (1.00 g, 5.26 mmol), using 3-chlorobenzyl bromide (0.76 ml, 5.80 mmol) according to the procedure for Intermediate 15. Purification by chromatography (30% EtOAc in hexane, silica) gave the title compound (833 mg, 50%). $\delta_H$ (CDCl$_3$) 8.50-8.47 (1H, m), 7.65 (1H, m), 7.45 (1H, s), 7.14-7.06 (3H, m), 6.91-6.90 (1H, m), 6.78-6.75 (1H, m), 5.69 (2H, s), 4.24 (2H, q, J 7.1 Hz), 1.26 (3H, t, J 7.1 Hz). LCMS (ES$^+$) RT 3.29 minutes, 315 [$^{35}$Cl]:317 [$^{37}$Cl] 3:1 (M+H$^+$).

Intermediate 25

Ethyl 1-(3-chlorobenzyl)-1H-pyrrolo[3,2-b]pyridine-2-carboxylate-4-oxide

From Intermediate 24 (830 mg, 2.64 mmol), using UHP (522 mg, 5.55 mmol) and TFAA (0.79 ml, 5.55 mmol) according to the procedure for Intermediate 16. Purification by chromatography (2%-10% MeOH in EtOAc, silica) gave the title compound (309 mg, 35%). $\delta_H$ (CDCl$_3$) 8.17-8.14 (1H, m), 7.69 (1H, s), 7.21-7.07 (4H, m), 6.96-6.82 (2H, m), 5.75 (2H, s), 4.29 (2H, q, J 7.1 Hz), 1.31 (3H, t, J 7.1 Hz). LCMS (ES$^+$) RT 2.38 minutes, 331 [$^{35}$Cl]:333 [$^{37}$Cl] 3:1 (M+H$^+$).

Intermediate 26

Ethyl 1-(3-chlorobenzyl)-5-oxo-4,5-dihydro-1H-pyrrolo[3,2-b]pyridine-2-carboxylate From Intermediate 25 (300 mg, 0.91 mmol) using TFAA (1.30 ml, 9.10 mmol) according to the procedure for Intermediate 17. The title compound required no further purification (372 mg, 100%). $\delta_H$ (CDCl$_3$) 7.25-7.15 (2H, m), 7.16 (1H, d, J 9.6 Hz). 6.96 (1H, s), 6.86-6.80 (2H, m), 6.46 (1H, d, J 9.6 Hz), 5.67 (2H, s), 4.24 (2H, q, J 7.1 Hz), 1.28 (3H, t, J 7.1 Hz). LCMS (ES$^+$) RT 3.19 minutes, 331 [$^{35}$Cl]:333 [$^{37}$Cl] 3:1 (M+H$^+$).

Intermediate 27

1-(3-Chloro-4-fluorobenzyl)-5-oxo-4-phenyl-4,5-dihydro-1H-pyrrolo[3,2-b]pyridine-2-carboxylic acid Example 24 (104 ng, 0.24 mmol) was treated with 1M sodium hydroxide (0.24 ml, 0.24 mmol) in EtOH (0.5 ml) under reflux for 4 hours. EtOH was removed in vacuo and the residue treated with 2M HCl, producing a white precipitate. This was collected by filtration, washed with water (1 ml) and Et$_2$O (1 ml), and dried in vacuo to give the title compound (80 mg, 82%) which required no further purification. $\delta_H$ (d$_6$-DMSO) 8.09 (1H, d, J 9.7 Hz), 7.64-7.42 (7H, m), 7.17-7.12 (1H, m), 6.55 (1H, d, J 9.7 Hz), 6.21 (1H, s), 5.88 (2H, s). LCMS (ES$^+$) RT 3.11 minutes, 397 [$^{35}$Cl]:399 [$^{37}$Cl] 3:1 (M+H$^+$).

Intermediate 28

1-(3-Methylbenzyl)-5-oxo-4-phenyl-4,5-dihydro-1H-pyrrolo[3,2-b]pyridine-2-carboxylic acid Example 25 (261 mg, 0.67 mmol) was treated with lithium hydroxide (85 mg, 2.02 mmol) in EtOH and water (2 ml each) at r.t. overnight, followed by reflux for 4 hours. EtOH was removed in vacuo and the residue treated with 2M HCl, producing a white precipitate. This was collected by filtration, washed with water (2 ml) and Et$_2$O (4 ml), and dried in vacuo to give the title compound (228 mg, 94%) which required no further purification $\delta_H$ (d$_6$-DMSO) 7.94 (1H d, J 9.7 Hz), 7.60-7.50 (3H, m), 7.47-7.39 (2H, m), 7.19 (1H, t, J 7.5 Hz), 7.06 (1H, d, J 8.7 Hz), 7.00 (1H, s), 6.86 (1H, d, J 7.3 Hz), 6.42 (1H, d, J 9.7 Hz), 6.09 (1H, s), 5.81 (2H, s), 2.26 (3H, s). LCMS (ES$^+$) RT 3.01 minutes, 359 (M+H$^+$).

Intermediate 29

1-(3-Chlorobenzyl)-5-oxo-4-phenyl-4,5-dihydro-1H-pyrrolo[3,2-b]pyridine-2-carboxylic acid Example 26 (310 mg, 0.76 mmol) was treated with lithium hydroxide (96 mg, 2.29 mmol) in EtOH and water (2 ml each) at r.t. overnight. EtOH was removed in vacuo and the residue treated with 2M HCl, producing a white precipitate. This was collected by filtration, washed with water (2 ml) and Et$_2$O (4 ml), and dried in vacuo to give the title compound (258 mg, 89%) which required no further purification. $\delta_H$ (d$_6$-DMSO) 8.22 (1H, d, J 9.7 Hz), 7.83-7.54 (7H, m), 7.46 (1H, s), 7.26-7.24 (1H, m), 6.68 (1H, d, J 9.7 Hz), 6.35 (1H, s), 6.06 (2H, s). LCMS (ES$^+$) RT 3.08 minutes, 379 [$^{35}$Cl]:381 [$^{37}$Cl] 3:1 (M+H$^+$).

Intermediate 30

1-(3-Chlorobenzyl)-4-(1H-indol-5-yl)-5-oxo-4,5-dihydro-1H-pyrrolo[3,2-b]pyridine-2-carboxylic acid 1M sodium hydroxide solution (0.75 ml, 0.75 mmol) was added to a suspension of Example 39 (243 mg, 0.55 mmol) in EtOH and water (2 ml each) and heated at reflux overnight. The reaction mixture was concentrated in vacuo giving the title compound (245 mg, 100%), which was used without further purification. $\delta_H$ (d$_6$-DMSO) 7.54 (1H, d, J 9.5 Hz), 7.46-7.37 (3H, m), 7.28-7.12 (4H, m), 6.90 (1H, dd, J 8.5, 2.0 Hz), 6.42 (1H, d, J 3.0 Hz), 6.05 (1H, d, J 9.5 Hz), 5.96 (1H, s), 5.67 (2H, s). LCMS (ES$^+$) RT 3.02 minutes, 418 [$^{35}$Cl]: 420 [$^{37}$Cl] 3:1 (M+H$^+$).

Intermediate 31

Ethyl 1-(4-fluoro-3-methylbenzyl)-1H-pyrrolo[3,2-b]pyridine-2-carboxylate

From Intermediate 14 (1.0 g, 5.26 mmol) using 4-fluoro-3-methylbenzyl bromide (1.18 g, 5.80 mmol) according to the procedure for Intermediate 15. Purification by chromatography (5%-10% EtOAc in DCM, silica) gave the title compound (670 mg, 40%). $\delta_H$ (CDCl$_3$) 8.61 (1H, d, J 4.4 Hz), 7.68 (1H, d, J 8.5 Hz), 7.55 (1H, s), 7.24 (1H, dd, J 4.4, 8.5 Hz), 6.96-6.81 (3H, m), 5.79 (2H, s), 4.39 (2H, q, J 7.1 Hz), 2.20 (3H, d, J 1.6 Hz), 1.41 (3H, t, J 7.1 Hz). LCMS (ES$^+$) RT 3.20 minutes, 313 (M+H$^+$).

Intermediate 32

Ethyl 1-(4-fluoro-3-methylbenzyl)-1H-pyrrolo[3,2-b]pyridine-2-carboxylate-4-oxide From Intermediate 31 (630 mg, 2.02 mmol) according to the procedure for Intermediate 16. Purification by chromatography (10% MeOH in EtOAc, silica) gave the title compound (680 mg, 100%). $\delta_H$ (CDCl$_3$) 8.23 (1H, d, J 6.0 Hz), 7.45 (1H, s), 7.32 (1H, d, J 8.5 Hz), 7.17 (1H, dd, J 6.0, 8.5 Hz), 6.97-6.84 (3H, m), 5.81 (2H, s), 4.40 (2H, q, J 7.1 Hz), 2.23 (3H, d, J 1.6 Hz), 1.41 (3H, t, J 7.1 Hz). LCMS (ES$^+$) RT 3.13 minutes, 329 (M+H$^+$).

Intermediate 33

Ethyl 1-(4-fluoro-3-methylbenzyl)-5-oxo-4,5-dihydro-1H-pyrrolo[3,2-b]pyridine-2-carboxylate From Intermediate 32 (680 mg, 2.07 mmol), according to the procedure for Intermediate 17. The title compound required no further purification (680 mg, 100%)-8H (CDCl$_3$)

8.16 (1H, d, J 9.7 Hz), 7.26-7.18 (2H, m), 7.04-6.99 (1H, m), 6.83 (1H, s), 6.47 (1H, d, J 9.7 Hz), 5.87 (2H, s), 4.42 (2H, q J 7.1 Hz), 2.33 (3H, s), 1.43 (3H, t, J 7.1 Hz). LCMS (ES$^+$) RT 3.29 minutes, 329 (M+H$^+$).

Intermediate 34

1-(Phenylsulfonyl)-4-(3-thienyl)-1,4-dihydro-5H-pyrrolo[3,2-b]pyridin-5-one

From Intermediate 3 (5.0 g, 18.2 mmol) using 3-thipheneboronic acid (5 g, 36.5 mmol) according to the procedure for Example 23. Purification by chromatography (5%-20% EtOAc in DCM, silica) gave the title compound (1.23 g, 19%). δ$_H$(d$_3$-MeOD) 8.28 (1H, d, J 9.7 Hz), 8.00 (2H, d, J 8.0 Hz), 7.74-7.68 (2H, m), 7.62-7.55 (4H, m), 7.11-7.08 (1H, m), 6.51 (1H, d, J 9.7 Hz), 6.09 (1H, d, J 3.6 Hz). LCMS (ES$^+$) RT 3.22 minutes, 357 (M+H$^+$).

Intermediate 35

4-(3-Thien 1)-1,4-dihydro-5H-pyrrolo[3,2-b]pyridin-5-one

From Intermediate 34 (1.20 g, 3.37 mmol), according to the method of Intermediate 5. The title compound required no further purification (680 mg, 94%). δ$_H$ (d$_3$-MeOD) 8.02 (1H, d, J 9.3 Hz), 7.87-7.82 (2H, m), 7.44-7.40 (2H, m), 6.61 (1H, d, J 9.3 Hz), 6.07-6.06 (1H, m). LCMS (ES$^+$) RT 2.44 minutes, 217 (M+H$^+$).

Intermediate 36

Ethyl 1-(2-cyanobenzyl)-H-pyrrolo[3,2-b]pyridine-2-carboxylate

From Intermediate 14 (1.0 g, 5.26 mmol) using 2-cyanobenzyl bromide (1.14 g, 5.80 mmol) according to the procedure for Intermediate 15. Purification by chromatography (5%-10% EtOAc in DCM, silica) gave the title compound (600 mg, 37%). δ$_H$(CDCl$_3$) 8.79 (1H, br s), 7.90-7.87 (1H, m), 7.79-7.76 (2H, m), 7.58-7.39 (3H, m), 6.73 (1H, d, J 7.6 Hz), 6.23 (2H, s), 4.53 (2H, q, J 7.1 Hz), 1.54 (3H, t, J 7.1 Hz). LCMS (ES$^+$) RT 2.92 minutes, 306 (M+H$^+$).

Intermediate 37

Ethyl 1-(2-cyanobenzyl)-1H-pyrrolo[3,2-b]pyridine-2-carboxylate 4-oxide

From Intermediate 36 (600 mg, 1.97 mmol) according to the method of Intermediate 16. Purification by chromatography (5%-10% MeOH in EtOAc, silica) gave the title compound (600 mg, 100%). δ$_H$ (CDCl$_3$) 8.02 (1H, d, J 6.0 Hz), 7.62 (1H, s), 7.54 (1H, d, J 7.5 Hz), 7.28-7.16 (2H, m), 7.04-6.94 (2H, m), 6.42 (1H, d, J 7.5 Hz), 5.88 (2H, s), 4.16 (2H, q, J 7.1 Hz), 1.17 (3H, t, J 7.1 Hz). LCMS (ES$^+$) RT 2.81 minutes, 322 (M+H$^+$).

Intermediate 38

Ethyl 1-(2-cyanobenzyl)-5-oxo-4,5-dihydro-1H-pyrrolo[3,2-b]pyridine-2-carboxylate From Intermediate 37 (680 mg, 2.07 mmol) according to the procedure for Intermediate 17. The title compound required no further purification (680 mg, 100%). δ$_H$ (CDCl$_3$) 7.74-7.81 (2H, m), 7.41 (1H, dt, J 7.7, 1.3 Hz), 7.27-7.32 (1H, m), 6.58 (1H, s), 6.27 (1H, d, J 7.7 Hz), 6.18 (1H, d, J 9.7 Hz), 5.81 (2H, s), 4.02 (2H, q, J 7.1 Hz), 1.04 (3H, t, J 7.1 Hz). LCMS (ES$^+$) RT 2.88 minutes, 322 (M+H$^+$).

Intermediate 39

Ethyl 1-(2-cyanobenzyl)-5-oxo-4-phenyl-4,5-dihydro-1H-pyrrolo[3,2-b]pyridine-2-carboxylate From Intermediate 38 (630 mg, 1.96 mmol), using phenylboronic acid (488 mg, 4.00 mmol), according to the procedure for Example 23. Purification by chromatography (10%-50% EtOAc in DCM, silica) gave the title compound (370 mg, 47%). δ$_H$(d$_3$-MeOD) 7.88 (1H, d, J 9.7 Hz), 7.75 (1H, dd, J 1.3, 7.6 Hz), 7.62-7.46 (4x, m), 7.40-7.36 (3H, m), 6.61 (1H, d, J 7.8 Hz), 6.55 (1H, d, J 9.7 Hz), 6.31 (1H, s), 6.01 (2H, s), 4.14 (2H, q, J 7.1 Hz), 1.14 (3H, t, J 7.1 Hz). LCMS (ES$^+$) RT 3.41 minutes, 398 (M+H$^+$).

Intermediate 40

1-(2-Cyanobenzyl)-5-oxo-4-phenyl-4,5-dihydro-1H-pyrrolo[3,2-b]pyridine-2-carboxylic acid From Intermediate 39 (337 mg, 0.85 mmol) according to the procedure of Intermediate 30. δ$_H$ (d$_6$-DMSO) 7.84 (1H, dd, J 1.1, 7.7 Hz), 7.65 (1H, d, J 9.5 Hz), 7.60-7.36 (7H, m), 6.47 (1H, d, J 7.7 Hz), 6.26 (2H, s), 6.14 (1H, d, J 9.5 Hz), 5.84 (1H, s). LCMS (ES$^+$) RT 2.80 minutes, 370 (M+H$^+$).

Intermediate 41

1-(4-Fluoro-3-methylbenzyl)-5-oxo-4-phenyl-4,5-dihydro-1H-pyrrolo[3,2-b]pyridine-2-carboxylic acid From Example 42 (541 mg, 1.34 mmol) according to the procedure of Intermediate 30. The title compound required no further purification (360 mg, 100%). δ$_H$ (d$_6$-DMSO) 7.76 (1H, d, J 9.5 Hz), 7.65-7.50 (3H, m), 7.42-7.40 (2H, m), 7.28 (1H, d, J 7.7 Hz), 7.17-7.06 (2H, m), 6.19 (1H, d, J 9.5 Hz), 6.03 (2H, s), 5.82 (1H, s), 2.23 (3H, s). LCMS (ES$^+$) RT 3.04 minutes, 377 (M+H$^+$).

Intermediate 42

1-(3-Chlorobenzyl)-4-(4-methylphenyl)-5-oxo-4,5-dihydro-1H-pyrrolo[3,2-b]pyridine-2-carboxylic acid From Example 44 (300 mg, 0.71 mmol) according to the procedure of Intermediate 30. The title compound required no fisher purification (315 mg, 100%). δ$_H$(d$_6$-DMSO) 7.95 (1H, d, J 9.5 Hz), 7.59-7.40 (8x, m), 6.48 (1H, d, J 9.5 Hz), 6.25 (2H, s), 5.99 (1H, s), 2.62 (3H, s). LCMS (ES$^+$) RT 3.16 minutes, 393 [$^{35}$Cl]:395 [$^{37}$Cl] 3:1 (M+H$^+$).

Intermediate 43

1-Benzyl-1H-pyrrolo[3,2-b]pyridine

A solution of 1H-pyrrolo[3,2-b]pyridine (1.30 g, 9.42 mmol) in DMF (15 ml) was treated with sodium hydride (60% in mineral oil, 434 mg, 11.3 mmol) at r.t. until effervescence ceased. After cooling to 0° C. benzyl bromide (1.68 ml, 14.1 mmol) was added and the reaction warmed at 60° C. overnight. The reaction mixture was partitioned between water and EtOAc (50 ml each) and extracted with EtOAc (50 ml). The combined organics were washed with brine (20 ml), dried (MgSO$_4$), filtered and concentrated in vacuo to give the title compound as a brown oil (1.20 g, 58%). $\delta_H$ (CDCl$_3$) 8.39 (1H, d, J 4.4 Hz), 7.48 (1H, d, J 8.2 Hz), 7.30 (1H, d, J 3.1 Hz), 7.26-7.18 (3H, m), 7.04-6.69 (3H, m), 6.67 (1H, d, J 4.4 Hz), 5.11 (2H, s). LCMS (ES$^+$) RT 1.56 ml 209 (M+H$^+$).

Intermediate 44

1-Benzyl-1H-pyrrolo[3,2-b]pyridine 4-oxide

From Intermediate 43 (1.20 g, 5.50 mmol) according to the procedure for Intermediate 9. The title compound required no further purification (1.23 g, 100%). $\delta_H$ (CDCl$_3$) 8.10 (11, d, J 6.0 Hz), 7.22-7.27 (5H, m), 7.10-7.09 (2H, m), 7.01-6.99 (2H, m), 5.25 (2H, s). LCMS (ES$^+$) RT 2.61 min. 225 (M+H$^+$).

Intermediate 45

1-Benzyl-3-(trifluoroacetyl)-1,4-dihydro-5H-pyrrolo[3,2-b]pyridin-5-one

A solution of Intermediate 44 (1.23 g, 5.50 mmol) in DMF (20 ml) was treated with TFAA (7.75 ml, 55.0 mmol) at 0° C. The reaction mixture was stirred at r.t. for 3 h. The reaction mixture was concentrated in vacuo, with use of a hot (approx 60° C.) water-bath. Purification by chromatography (80% EtOAc in hexane to neat EtOAc, silica) gave the title compound (560 mg, 45%). $\delta_H$ (CDCl$_3$) 7.88 (1H, s), 7.52 (1H, d, J 2.0 Hz), 7.30-7.25 (3H, m), 7.05-7.03 (2H, m), 6.36 (1H, d, J 9.0 Hz), 5.16 (2H, s). LCMS (ES$^+$) RT 3.12 min, 321 (M+H$^+$).

EXAMPLE 1

1-Benzyl-4-phenyl-1,4-dihydro-5H-pyrrolo[3,2-b]pyridin-5-one

Intermediate 5 (140 mg, 0.67 mmol) was added to sodium hydride (60% suspension in mineral oil, 53 mg, 1.33 mmol) suspended in THF (2 ml). Benzyl chloride (125 mg, 0.73 mmol) was added and the reaction stirred at r.t. for 30 minutes. The reaction mixture was concentrated in vacuo and purification by chromatography (gradient elution DCM-EtOAc, silica) gave the title compound (168 mg, 84%). $\delta_H$ (CDCl$_3$) 7.56 (2H, m), 7.46 (4H, m), 7.38 (3H, m), 7.17 (2H, m), 6.92 (1H, d, J 3.0 Hz), 6.44 (1H, d, J 9.5 Hz), 5.68 (1H, d, J 2.7 Hz), 5.25 (2H, s). LCMS (ES$^+$) RT 3.241 minutes, 301 (M+H$^+$).

EXAMPLES 2 TO 5

The compounds of Examples 2-5 were made by a similar procedure to the compound of Example 1, using Intermediate 5 and the appropriate substituted benzyl chloride.

EXAMPLE 2

1-(3-Chlorobenzyl)-4-phenyl-1,4-dihydro-5H-pyrrolo[3,2-b]pyridin-5-one $\delta_H$ (CDCl$_3$) 7.49 (2H, m), 7.36 (4H, m), 7.23 (2H, m), 7.06 (1H, d, J 0.7 Hz), 6.94 (1H, m), 6.84 (1H, d, J 3.0 Hz), 6.36 (1H, d, J 9.6 Hz), 5.61 (11, dd, J 0.6, 3.0 Hz), 5.12 (2H, s). LCMS (ES$^+$) RT 3.418 minutes, 335 (M+H$^+$).

EXAMPLE 3

1-(4-Fluorobenzyl)-4-phenyl-1,4-dihydro-5H-pyrrolo[3,2-b]pyridin-5-one $\delta_H$ (CDCl$_3$) 7.48 (2H, m), 7.37 (4×, m), 7.09 (2×, m), 7.00 (2H, m), 6.83 (1H, d, J 3.0 Hz), 6.37 (1H, d, J 9.5 Hz), 5.61 (1H, d, J 3.0 Hz), 5.14 (2H, s). LCMS (ES$^+$) RT 3.252 minutes, 319 (M+H)$^+$.

EXAMPLE 4

1-(2,6-Dichlorobenzyl)-4-phenyl-1,4-dihydro-5H-pyrrolo[3,2-b]pyridin-5-one $\delta_H$ (CDCl$_3$) 7.61 (1H, d, J 9.5 Hz), 7.43 (2H, m), 7.32 (5H, m), 7.21 (1H, m), 6.65 (1H, d, J 3.1 Hz), 6.40 (1H, d, J 9.5 Hz), 5.49 (1H, d, J 3.1 Hz), 5.38 (2H, s). LCMS (ES$^+$) RT 3.552 minutes, 369 (M+H)$^+$.

EXAMPLE 5

1-(3-Methoxybenzyl)-4-phenyl-1,4-dihydro-5H-pyrrolo[3,2-b]pyridin-5-one $\delta_H$ (CDCl$_3$) 7.48-7.46 (2H, m), 7.45-7.34 (4H, m), 7.23-7.19 (1H, m), 6.83 (1H, d, J 3.0 Hz), 6.78 (1H, dd, J 2.4, 8.3 Hz), 6.66 (1H, d, J 7.6 Hz), 6.60 (1H, s), 6.34 (1H, d, J 9.5 Hz), 5.58 (1H, d, J 3.0 Hz), 5.11 (2H, s), 3.71 (3H, s). LCMS (ES$^+$) RT 3.239 minutes, 331 (M+H)$^+$.

EXAMPLE 6

1-Benzyl-4-(4-methoxyphenyl)-1,4-dihydro-5H-pyrrolo[3,2-b]pyridin-5-one

The title compound (9 mg) was prepared in a similar manner to the compound of Example 1 from Intermediate 7 (30 mg, 0.125 mmol) and benzyl chloride (18 mg, 0.14 mmol). $\delta_H$ (CDCl$_3$) 7.34 (1H, d, J 7.7 Hz), 7.28 (5H, m), 7.10 (2H, d, J 4.4 Hz), 6.98 (2H, d, J 6.6 Hz), 6.82 (1H, d, J 2.2 Hz), 6.33 (1H, d, J 7.7 Hz), 5.60 (1H, d, J 2.2 Hz), 5.15 (2H, s), 3.80 (3H, s). LCMS (ES$^+$) RT 3.304 minutes, 331 (M+H)$^+$.

EXAMPLE 7

1-Benzoyl-4-phenyl-1,4-dihydro-5H-pyrrolo[3,2-b]pyridin-5-one

The title compound (146 mg) was prepared, in a similar manner to Intermediate 4, from Intermediate 10. $\delta_H$ (d$_6$-DMSO) 8.32 (1H, d, J 9.8 Hz), 7.75 (3H, m), 7.59 (5H, m), 7.40 (2H, dd, J 1.5, 8.4 Hz), 7.30 (1H, d, J 3.7 Hz), 6.43 (1H, d, J 9.8 Hz), 5.81 (1H, dd, J 0.3, 4.1 Hz). LCMS (ES$^+$) RT 3.299 minutes, 315 (M+H)$^+$.

EXAMPLE 8

4-[(5-Oxo-4-phenyl-4,5-dihydro-1H-pyrrolo[3,2-b]pyridin-1-yl)methyl]benzonitrile From Intermediate 5 (150 mg, 0.71 mmol) and 4-cyanobenzyl bromide (139 mg, 0.71 mmol) according to the procedure for Example 6, to give the title compound (151 mg, 65%). $\delta_H$ (d$_6$-DMSO) 7.59 (2H, d, J 8.2 Hz), 7.50-7.45 (2H, m), 7.41-7.34 (3H, m), 7.26 (1H, d, J 9.1 Hz), 7.13 (2H, d, J 8.1 Hz), 6.83 (1H, d, J 3.0 Hz), 6.35 (1H, d, J 9.5 Hz), 5.64 (1H, d, J 2.7 Hz), 5.21 (2H, s). LCMS (ES$^+$) RT 3.018 minutes, 326 (M+H$^+$).

EXAMPLE 9

3-[(5-Oxo-4-phenyl-4,5-dihydro-1H-pyrrolo[3,2-b]pyridin-1-yl)methyl]benzonitrile From Intermediate 5 (150 mg, 0.71 mmol) and 3-cyanobenzyl bromide (139 mg, 0.71 mmol) according to the procedure for Example 6, to give the title compound (148 mg, 64%). $\delta_H$ (CDCl$_3$) 7.55 (1H, d, J 7.7 Hz), 7.50-7.36 (6H, m), 7.33 (1H, s), 7.28 (2H, d, J 9.0 Hz), 6.83 (1H, d, J 3.0 Hz), 6.36 (1H, d, J 9.6 Hz), 5.65 (1H, dd, J 1.3, 2.4 Hz), 5.19 (2H, s). LCMS (ES$^+$) RT 3.021 minutes, 326 (M+H$^+$).

EXAMPLE 10

1-(2-Methylbenzyl)-4-phenyl-1,4-dihydro-5H-pyrrolo[3,2-b]pyridin-5-one

From Intermediate 5 (150 mg, 0.71 mmol) and 2-methylbenzyl bromide (131 mg, 0.71 mmol) according to the procedure for Example 6, to give the title compound (129 mg, 58%). $\delta_H$ (CDCl$_3$) 7.59-7.54 (2H, m), 7.49-7.45 (4H, m), 7.30-7.19 (3H, m), 6.88 (1H, d, J 7.5 Hz), 6.79 (1H, d, J 3.0 Hz), 6.44 (1H, d, J 9.5 Hz), 5.66 (1H, d, J 3.0 Hz), 5.22 (2H, s), 2.33 (3H, s). LCMS (ES$^+$) RT 3.373 minutes, 315 (M+H$^+$).

EXAMPLE 11

1-(3-Methylbenzyl)-4-phenyl-1,4-dihydro-5H-pyrrolo[3,2-b]pyridin-5-one

From Intermediate 5 (150 mg, 0.71 mmol) and 3-methylbenzyl bromide (131 mg, 0.71 mmol) according to the procedure for Example 6, to give the title compound (146 mg, 65%). $\delta_H$ (CDCl$_3$) 7.58-7.54 (2H, m), 7.48-7.44 (4H, m), 7.29-7.25 (1H, m), 7.15 (1H, d, J 7.6 Hz), 7.00-6.96 (2H, m), 6.91 (1H, d, J 3.0 Hz), 6.43 (1H, d, J 9.5 Hz), 5.67 (1H, d, J 3.0 Hz), 5.20 (2H, s), 2.37 (3H, s). LCMS (ES$^+$) RT 3.363 minutes, 315 (M+H$^+$).

EXAMPLE 12

1-(4-Methylbenzyl)-4-phenyl-1,4-dihydro-5H-pyrrolo[3,2-b]pyridin-5-one

From Intermediate 5 (150 mg, 0.71 mmol) and 4-methylbenzyl bromide (131 mg, 0.71 mmol) according to the procedure for Example 6, to give the title compound (142 mg, 64%). $\delta_H$ (CDCl$_3$) 7.48-7.44 (2H, m), 7.39-7.34 (4H, m), 7.09 (2H, d, J 7.9 Hz), 6.98 (2H, d, J 8.2 Hz), 6.81 (1H, d, J 3.0 Hz), 6.33 (1H, d, J 9.4 Hz), 5.57 (1H, dd, J 0.6, 3.0 Hz), 5.10 (2H, s), 2.27 (3H, s). LCMS (ES$^+$) RT 3.376 minutes, 315 (M+H$^+$).

EXAMPLE 13

1-(4-Chlorobenzyl)-4-phenyl-1,4-dihydro-5H-pyrrolo[3,2-b]pyridin-5-one

From Intermediate 5 (150 mg, 0.71 mmol) and 4-chlorobenzyl bromide (146 mg, 0.71 mmol) according to the procedure for Example 6, to give the title compound (158 mg, 67%). $\delta_H$ (CDCl$_3$) 7.57-7.54 (2H, m), 7.49-7.34 (6H, m), 7.09 (2H, d, J 8.3 Hz), 6.90 (1H, d, J 3.0 Hz), 6.43 (1H, d, J 9.5 Hz), 5.69 (1H, d, J 3.0 Hz), 5.21 (2H, s). LCMS (ES$^+$) RT 3.383 minutes, 335 (M+H$^+$).

EXAMPLE 14

1-(3,4-Dichlorobenzyl)-4-phenyl-1,4-dihydro-5H-pyrrolo[3,2-b]pyridin-5-one

From Intermediate 5 (150 mg, 0.71 mmol) and 3,4-dichlorobenzyl bromide (170 mg, 0.71 mmol) according to the procedure for Example 6, to give the title compound (173 mg, 66%). $\delta_H$ (CDCl$_3$) 7.59-7.55 (2H, m), 7.49-7.43 (5H, m), 7.41-7.26 (1H, m), 6.97 (1H, dd, J 2.1, 8.2 Hz), 6.90 (1H, d, J 3.0 Hz), 6.45 (1H, d, J 9.6 Hz), 5.71 (1H, d, J 3.0 Hz), 5.20 (2H, s). LCMS (ES$^+$) RT 3.531 minutes, 369 (M+H$^+$).

EXAMPLE 15

1-(2,5-Dichlorobenzyl)-4-phenyl-1,4-dihydro-5H-pyrrolo[3,2-b]pyridin-5-one

From Intermediate 5 (150 mg, 0.71 mmol) and 2,5-dichlorobenzyl bromide (170 mg, 0.71 mmol) according to the procedure for Example 6, to give the title compound (147 mg, 40%). $\delta_H$ (CDCl$_3$) 7.62-7.52 (2H, m), 7.50-7.36 (5H, m), 7.30-7.27 (1H, m), 6.92 (1H, d, J 3.0 Hz), 6.78 (1H, d, J 3.4 Hz), 6.48 (11, d, J 9.5 Hz), 5.74 (1H, d, J 3.0 Hz), 5.31 (2H, s). LCMS (ES$^+$) RT 3.525 minutes, 369 (M+H$^+$).

EXAMPLE 16

1-(3,4-Difluorobenzyl)-4-phenyl-1,4-dihydro-5H-pyrrolo[3,2-b]pyridin-5-one

From Intermediate 5 (150 mg, 0.71 mmol) and 3,4-difluorobenzyl bromide (147 mg, 0.71 mmol) according to the procedure for Example 6, to give the title compound (154 mg, 64%). $\delta_H$ (CDCl$_3$) 7.59-7.54 (2H, m), 7.50-7.39 (4H, m), 7.22-7.15 (1H, m), 7.02-6.89 (3H, m), 6.45 (1H, d, J 9.5 Hz), 5.71 (1H, d, J 3.0 Hz), 5.20 (2H, s). LCMS (ES$^+$) RT 3.241 minutes, 337 (M+H$^+$).

EXAMPLE 17

1-(2,4-Difluoro)-4-phenyl-1,4-dihydro-5H-pyrrolo[3,2-b]pyridin-5-one

From Intermediate 5 (150 mg, 0.71 mmol) and 2,4-difluorobenzyl bromide (147 mg, 0.71 mmol) according to the procedure for Example 6, to give the title compound (138 mg, 58%). $\delta_H$ (CDCl$_3$) 7.57-7.48 (3H, m), 7.47-7.41 (3H, m), 7.05-7.01 (1H, m), 6.99-6.86 (3H, m), 6.47 (1H, d, J 9.5 Hz), 5.68 (1H, d, J 2.9 Hz), 5.24 (2H, s). LCMS (ES$^+$) RT 3.257 minutes, 337 (M+H$^+$).

EXAMPLE 18

1-(3-Chloro-4-fluorobenzyl)-4-phenyl-1,4-dihydro-5H-pyrrolo[3,2-b]pyridin-5-one From Intermediate 5 (150 mg, 0.71 mmol) and 3-chloro-4-fluorobenzyl bromide (159 mg, 0.71 mmol) according to the procedure for Example 6, to give the title compound (148 mg, 59%). $\delta_H$ (d$_6$-DMSO) 7.68-7.64 (2H, m), 7.59-7.49 (4H, m), 7.33-7.30 (1H, m), 7.25 (1H, t, J 8.6 Hz), 7.14-7.10 (1H, m), 7.00 (1H, d, J 3.0 Hz), 6.55 (1H, d, J 9.5 Hz), 5.80 (1H, dd, J 0.5, 3.0 Hz), 5.29 (2H, s). LCMS (ES$^+$) RT 3.394 minutes, 353 (M+H$^+$).

EXAMPLE 19

4-Phenyl-1-(pyridin-4-methyl)-1,4-dihydro-5H-pyrrolo[3,2-b]pyridin-5-one

Intermediate 5 (125 mg, 0.6 mmol) in THF (5 ml) was treated with sodium hydride (60% dispersion in mineral oil, 60 mg, 1.5 mmol), 4-chloromethylpyridine hydrochloride (98.5 mg, 0.6 mmol) and DMSO (1 ml). The reaction was stirred at r.t. for 2 h then warmed to 60° C. for 30 minutes. After quenching with water the product was extracted into DCM, dried ($Na_2SO_4$) and concentrated in vacuo. Chromatography (10% MeOH in EtOAc, silica) gave the title compound (68 mg, 38%). $\delta_H$ ($CDCl_3$) 8.54 (2H, dd, J 1.6, 4.5 Hz), 7.50-7.46 (2H, m), 7.41-7.36 (3H, m), 7.27 (1H, d, J 9.6 Hz), 6.93 (2H, m), 6.84 (1H, d, J 3.0 Hz), 6.36 (1H, d, J 9.5 Hz), 5.65 (1H, d, J 3.0 Hz), 5.15 (2H, s). LCMS ($ES^+$) RT 1.822 minutes, 302 ($M+H^+$).

EXAMPLE 20

4-Phenyl-1-(pyridin-3-ylmethyl)-1,4-dihydro-5H-pyrrolo[3,2-b]pyridin-5-one

From Intermediate 5 (125 mg, 0.6 mmol), 3-chloromethylpyridine hydrochloride (98.5 ng, 0.6 mmol) and sodium hydride (60% in mineral oil, 60 mg, 1.5 mmol), by the method of Example 19, to give the title compound (57 mg, 32%). $\delta_H$ ($CDCl_3$) 8.62 (1H, dd, J 1.4, 4.7 Hz), 8.54 (1H, d, J 2.0 Hz), 7.58-7.54 (2H, m), 7.49-7.42 (5H, m), 7.34-7.30 (1H, m), 6.92 (1H, d, J 3.0 Hz), 6.46 (1H, d, J 9.6 Hz), 5.71 (1H, d, J 3.0 Hz), 5.27 (2H, s). LCMS ($ES^+$) RT 2.220 minutes, 302 ($M+H^+$).

EXAMPLE 21

4-Phenyl-1-(1-phenylethyl)-1,4-dihydro-5H-pyrrolo[3,2-b]pyridin-5-one

From Intermediate 5 (125 mg, 0.6 mmol), α-methylbenzyl bromide (111 mg, 0.6 mmol) and sodium hydride (60% in mineral oil, 31 mg, 0.78 mmol) by the method of Example 19 to give the title compound (76 mg, 40%). $\delta_H$ ($CDCl_3$) 7.58-7.54 (2H, m), 7.49-7.44 (3H, m), 7.41-7.31 (4H, m), 7.18-7.16 (2H, m), 7.08 (1H, d, J 3.1 Hz), 6.37 (1H, d, J 9.5 Hz), 5.70 (1H, d, J 3.1 Hz), 5.54 (1H, q, J 7.1 Hz), 1.92 (3H, d, J 7.06 Hz). LCMS ($ES^+$) RT 3.320 minutes, 315 ($M+H^+$).

EXAMPLE 22

1-(3-Chlorobenzyl)-4-phenyl-2-(pyrrolidin-1-ylsulfonyl)-1,4-dihydro-5H-pyrrolo[3,2-b]pyridin-5-one Intermediate 12 (140 mg, 0.408 mmol) in THF (10 ml) was treated with sodium hydride (60% dispersion in mineral oil, 19.5 mg, 0.49 mmol) under nitrogen at r.t. After stirring for 10 minutes 3-chlorobenzyl bromide (84.3 mg, 0.41 mmol) was added and the reaction stirred for 3 h. After 3 h TLC showed little change so further sodium hydride (60% dispersion in mineral oil, 20 mg, 0.41 mmol) was added followed by DMSO (1 ml), and the reaction heated at 70° C. for 1 h then at r.t. overnight. The reaction was partitioned between water and DCM, and the organic phase separated, dried ($Na_2SO_4$), and concentrated in vacuo. Purification by chromatography (EtOAc-silica) gave the title compound (62 mg, 33%). $\delta_H$ ($d_6$-DMSO) 7.88-7.85 (1H, m), 7.63-7.58 (2H, m), 7.54-7.50 (1H, m), 7.47-7.44 (2H, m), 7.39-7.34 (2H, m), 7.22 (1H, s), 6.97-6.94 (1H, m), 6.48 (1H, d, J 9.8 Hz), 6.07 (1H, s), 5.71 (2H, s), 3.09-3.04 (4H, m), 1.65-1.60 (4H, m). LCMS ($ES^+$) RT 3.283 minutes, 468 ($M+H^+$).

EXAMPLE 23

Ethyl 1-benzyl-5-oxo-4-phenyl-4,5-dihydro-1H-pyrrolo[3,2-b]pyridine-2-carboxylate Phenylboronic acid (47 nag, 0.37 mmol), pyridine (0.05 ml, 0.57 mmol) and copper(II) acetate (69 mg, 0.37 mmol) were added to a suspension of Intermediate 17 (57 mg, 0.19 mmol) in DCM (2 ml). The reaction mixture was stirred overnight at r.t. The reaction mixture was diluted with DCM (20 ml), washed with 2M HCl, dried ($MgSO_4$) and concentrated in vacuo. Purification by chromatography (10%-20% EtOAc in DCM) gave the title compound (44 mg, 62%). $\delta_H$ ($CDCl_3$) 7.20-7.60 (9H, m), 7.04-7.00 (2H, m), 6.51 (1H, d, J 9.7 Hz), 6.30 (1H, d, J 0.6 Hz), 5.71 (2H, s), 4.18 (2H, q, J 7.1 Hz), 1.20 (3H, t, J 7.1 Hz). LCMS Method C ($ES^+$) RT 2.44 minutes, 373 ($M+H^+$).

EXAMPLE 24

Ethyl 1-(3-chloro-4-fluorobenzyl)-5-oxo-phenyl-4,5-dihydro-1H-pyrrolo[3,2-b]pyridine-2-carboxylate From Intermediate 20 (880 mg, 2.53 mmol), phenylboronic acid (617 mg, 5.06 mmol), pyridine (0.61 ml, 7.59 mmol) and copper(II) acetate (920 mg, 5.06 mmol) according to the procedure for Example 23. Purification by chromatography (15% EtOAc in DCM, silica) gave the title compound (630 mg, 59%). $\delta_H$ ($CDCl_3$) 7.45-7.25 (6H m), 7.03-6.76 (3H, m), 6.49 (1H, d, J 9.7 Hz), 6.24 (1H, s), 5.56 (2H, s), 4.11 (2H, q, J 7.1 Hz), 1.14 (311, t, J 7.1 Hz). LCMS ($ES^+$) RT 3.83 minutes, 425 [$^{35}Cl$]:427 [$^{37}Cl$] 3:1 ($M+H^+$).

EXAMPLE 25

Ethyl 1-(3-methylbenzyl)-5-oxo-4-phenyl-4,5-dihydro-1H-pyrrolo[3,2-b]pyridine-2-carboxylate From Intermediate 23 (354 mg, 1.14 mmol), phenylboronic acid (278 mg, 2.28 mmol), pyridine (0.28 ml, 3.42 mmol) and copper(II) acetate (414 mg, 2.28 mmol) according to the procedure for Example 23. Purification by chromatography (15% EtOAc in DCM, silica) gave the title compound (348 mg, 79%). $\delta_H$ ($CDCl_3$) 7.57-7.34 (6H, m), 7.15-7.10 (1H, m), 7.00 (1H, d, J 7.6 Hz), 6.84 (1H, s), 6.78 (1H, d, J 7.6 Hz), 6.52 (1H, d, J 9.5 Hz), 6.30 (1H, s), 5.67 (2H, s), 4.18 (2H, q, J 7.1 Hz), 2.24 (3H, s), 1.20 (3H, t, J 7.1 Hz). LCMS ($ES^+$) RT 3.77 minutes, 387 ($M+H^+$).

EXAMPLE 26

Ethyl 1-(3-chlorobenzyl)-5-oxo-4-phenyl-4,5-dihydro-1H-pyrrolo[3,2-b]pyridine-2-carboxylate From Intermediate 26 (300 mg, 0.91 mmol), phenylboronic acid (222 mg, 1.82 mmol), pyridine (0.22 ml, 2.73 mmol) and copper(II) acetate (330 mg, 1.82 mmol) according to the procedure for Example 23. Purification by chromatography (15% EtOAc in DCM, silica) gave the title compound (317 mg, 86%). $\delta_H$ ($CDCl_3$) 7.50-7.31 (6H, m), 7.16-7.14 (2H, m), 6.97 (1H, s), 6.87-6.85 (1H, m), 6.51 (1H, d, J 9.7 Hz), 6.28 (1H, s), 5.64 (2H, s), 4.15 (2H, q, J 7.1 Hz), 1.17 (3H, t, J 7.1 Hz). LCMS ($ES^+$) RT 3.80 minutes, 407 [$^{35}Cl$]: 409 [$^{37}Cl$] 3:1 ($M+H^+$).

EXAMPLE 27

1-(3-Chloro-4-fluorobenzyl)-N-methoxy-N-methyl-5-oxo-4-phenyl-4,5-dihydro-1H-pyrrolo[3,2-b]pyridine-2-carboxamide A suspension of Intermediate 27 (110 mg, 0.28 mmol) in DCM (2 ml) was treated with EDC (80 mg, 0.42 mmol), N,O-dimethylhydroxylamine (41 mg, 0.42 mmol) and triethylamine (0.12 ml, 0.84 mmol). The reaction was stirred at r.t. overnight. The reaction mixture was diluted with DCM (20 ml), washed with 2M HCl, dried (MgSO$_4$) and concentrated in vacuo. Purification by chromatography (20% EtOAc in DCM, silica) gave the title compound (36 mg, 29%). $\delta_H$ (CDCl$_3$) 7.48-7.34 (6H, m), 7.12-6.91 (3H, m), 6.52 (1H, d, J 9.7 Hz), 6.23 (1H, s), 5.52 (2H, s), 3.40 (3H, s), 3.18 (3H, s). LCMS (ES$^+$) RT 3.37 minutes, 440 [$^{35}$Cl]:442 [$^{37}$Cl] 3:1 (M+H$^+$).

EXAMPLE 28

N-Methoxy-N-methyl-1-(3-methylbenzyl)-5-oxo-4-phenyl-4,5-dihydro-1H-pyrrolo[3,2-b]pyridine-2-carboxamide From Intermediate 28 (29 mg, 0.08 mmol), using EDC (23 mg, 0.12 mmol), N,O-dimethylhydroxylamine (12 mg, 0.12 mmol) and triethylamine (0.034 nil, 0.24 mmol), according to the procedure of Example 27. Purification by chromatography (20% EtOAc in DCM, silica) gave the title compound (11 mg, 34%). $\delta_H$ (CDCl$_3$) 7.50-7.33 (6H, m), 7.19-7.11 (1H, m), 6.99 (1H, d, J 7.6 Hz), 6.87 (1H, s), 6.79 (1H, d, J 7.6 Hz), 6.48 (1H, d, J 9.7 Hz), 6.15 (1H, s), 5.52 (2H, s), 3.34 (3H, s), 3.15 (3H, s), 2.23 (3H, s). LCMS (ES$^+$) RT 3.27 minutes, 402 (M+H$^+$).

EXAMPLE 29

1-(3-Chlorobenzyl)-N-methoxy-N-methyl-5-oxo-4-phenyl-4,5-dihydro-1H-pyrrolo[3,2-b]pyridine-2-carboxamide From Intermediate 29 (56 mg, 0.15 mmol), using EDC (43 mg, 0.23 mmol), N,O-dimethylhydroxylamine (22 mg, 0.23 mmol) and triethylamine (0.06 ml, 0.45 mmol), according to the procedure of Example 27. Purification by chromatography (20% EtOAc in DCM, silica) gave the title compound (21 mg, 34%). $\delta_H$ (CDCl$_3$) 7.50-7.33 (5H, m), 7.19-7.16 (3H, m), 7.02 (1H, s), 6.94-6.91 (1H, m), 6.50 (1H, d, J 9.6 Hz), 6.21 (1H, s), 5.55 (2H, s), 3.38 (3H, s), 3.17 (3H, s). LCMS (ES$^+$) RT 3.33 minutes, 422 [$^{35}$Cl]:424 [$^{37}$Cl] 3:1 (M+H$^+$).

EXAMPLE 30

1-(3-Chloro-4-fluorobenzyl)-5-oxo-4-phenyl-4,5-dihydro-1H-pyrrolo[3,2-b]pyridine-2-carboxamide A suspension of Intermediate 27 (100 mg, 0.25 mmol) in DMF (1 ml) was treated with CDI (50 mg, 0.30 mmol) and stirred at room temperature for 1 h. Ammonia 880 (1 ml) was added and the reaction mixture stirred at r.t. for 1 h. The reaction mixture was partitioned between DCM and water (30 ml each) and the organics dried (MgSO$_4$) and concentrated in vacuo. Purification by chromatography (5% THF in EtOAc, silica) gave the title compound (65 mg, 65%). $\delta_H$ (d$_6$-DMSO) 7.75 (1H, d, J 9.6 Hz), 7.69 (1H, br s), 7.38-7.01 (8H, m), 6.93-6.90 (1H, m), 6.19 (1H, s), 6.15 (1H, d, J 9.6 Hz), 5.63 (2H, s). LCMS (ES$^+$) RT 2.98 minutes, 396 [$^{35}$Cl]: 398 [$^{37}$Cl] 3:1 (M+H$^+$).

EXAMPLE 31

1-(3-Methylbenzyl)-5-oxo-4-phenyl-4,5-dihydro-1H-pyrrolo[3,2-b]pyridine-2-carboxamide From Intermediate 28 (200 ng, 0.56 mmol) according to the procedure for Example 30. Purification by chromatography (5% THF in EtOAc, silica) gave the title compound (100 mg, 50%). $\delta_H$ (d$_6$-DMSO) 7.94-7.87 (2H, m), 7.62-7.44 (5H, m), 7.30-7.24 (2H, m), 7.12-7.07 (2H, m), 6.94 (1H, d, J 7.5 Hz), 6.43 (1H, s), 6.39 (1H, d, J 9.6 Hz), 5.90 (2H, s), 2.31 (3H, s). LCMS (ES$^+$) RT 2.91 minutes, 358 (M+H$^+$).

EXAMPLE 32

1-(3-Chlorobenzyl)-5-oxo-4-phenyl-4,5-dihydro-1H-pyrrolo[3,2-b]pyridine-2-carboxamide From Intermediate 29 (200 mg, 0.53 mmol) according to the procedure for Example 30. Purification by chromatography (5% THF in EtOAc, silica) gave the title compound (75 mg, 38%). $\delta_H$ (d$_6$-DMSO) 8.00-7.92 (2H, m), 7.67-7.53 (3H, m), 7.48-7.29 (6H, m), 7.16-7.11 (1H, m), 6.47 (1H, s), 6.42 (1H, d, J 9.6 Hz), 5.93 (2H, s). LCMS (ES$^+$) RT 2.95 minutes, 378 [$^{35}$Cl]:380 [$^{37}$Cl]3:1 (M+H$^+$).

EXAMPLE 33

4-Phenyl-1-(2-phenylethyl)-1,4-dihydro-5H-pyrrolo[3,2-b]pyridin-5-one

A solution of Intermediate 5 (210 mg, 1.00 mmol) in THF and DMF (5 ml each) was treated with sodium hydride (60% in mineral oil, 200 mg, 5.00 mmol) at r.t. 2-Phenylethyl bromide (0.68 ml, 5.00 mmol) was added and the reaction stirred at r.t. overnight. The reaction mixture was partitioned between water (30 ml) and EtOAc (40 ml), washed with brine (20 ml), dried (MgSO$_4$) and concentrated in vacuo. Purification by chromatography (50% EtOAc in DCM, silica) gave the title compound (218 mg, 68%). $\delta_H$ (CDCl$_3$) 7.82-7.52 (9H, m), 7.32-7.30 (2H, m), 6.94 (1H, d, J 2.8 Hz), 6.66 (1H, d, J 9.5 Hz), 5.79 (1H, d, J 2.8 Hz), 4.49 (2H, t, J 7.1 Hz), 3.32 (2H, t, J 7.1 Hz). LCMS (ES$^+$) RT 3.34 minutes, 315 (M+H$^+$).

EXAMPLE 34

1-(3-Chlorobenzyl)-5-oxo-4-phenyl-4,5-dihydro-1H-pyrrolo[3,2-b]pyridine-2-carbonitrile A suspension of Example 32 (200 mg, 0.53 mmol) in DCM (2 ml) was treated with pyridine (0.11 ml 1.06 mmol) followed, after a few minutes, by TFAA (0.09 ml, 0.64 mmol). The reaction was stirred at r.t. for 15 minutes. EtOH (2 ml) was added and stirred for 5 minutes prior to removal of solvents in vacuo. The residue was dissolved in DCM (15 ml) and washed with copper(II) sulfate (2×10 ml), dried (MgSO$_4$) and concentrated in vacuo to give the title compound (175 mg, 92%). $\delta_H$ (d$_3$-MeOD) 7.87 (1H, d, J 9.7 Hz), 7.55-7.43 (3H, m), 7.32-7.23 (4H, m), 7.18 (1H, s), 7.06-7.03 (1H, m), 6.55 (1H, d, J 9.7 Hz), 6.25 (1H, s), 5.45 (2H, s). LCMS (ES$^+$) RT 3.43 minutes, 360 [$^{35}$Cl]:362 [$^{37}$Cl] 3:1 (M+H$^+$).

EXAMPLE 35

1-(3-Chlorobenzyl)-N,N-dimethyl-5-oxo-4-phenyl-4,5-dihydro-1H-pyrrolo[3,2-b]pyridine-2-carboxamide A solution of Intermediate 29 (400 mg, 1.00 mmol) in DMF (5 ml) was treated sequentially with thionyl chloride (0.15 ml, 2.00 mmol), then 2M dimethylamine in THF (1.5 ml, 3.00 mmol). The reaction mixture was stirred at r.t. for 15 minutes. Water (20 ml) was added and the mixture extracted with DCM (2×20 ml), dried (MgSO$_4$), concentrated in vacuo and purified by chromatography (EtOAc, silica) to give the title compound (200 mg, 50%). $\delta_H$ (d$_3$-MeOD) 7.86 (1H, d, J 9.5 Hz), 7.52-7.40 (3H, m), 7.33-7.31 (2H, m), 7.23-7.18 (2H, m), 7.10 (1H, s), 7.09-6.98 (1H, br m), 6.42 (1H, d, J 9.5 Hz), 5.77 (1H, s), 5.38 (2H, s), 2.95-2.83 (6H, br m). LCMS (ES$^+$) RT 3.12 minutes, 406 [$^{35}$Cl]:408 [$^{37}$Cl] 3:1 (M+H$^+$).

EXAMPLE 36

1-(3-Chlorobenzyl)-N-methyl-5-oxo-4-phenyl-4,5-dihydro-1H-pyrrolo[3,2-b]pyridine-2-carboxamide From Intermediate 29 (400 mg, 1.00 mmol), using methylamine hydrochloride (203 mg, 3.00 mmol) and triethylamine (0.42 ml, 3.00 mmol), according to the procedure for Example 35. Purification by chromatography (EtOAc, silica) gave the title compound (104 mg, 27%). $\delta_H$ (d$_3$-MeOD) 7.92 (1H, dd, J 0.5, 9.5 Hz), 7.67-7.53 (3H, m), 7.46-7.43 (2H, m), 7.33-7.25 (2H, m), 7.17 (1H, s), 7.08-7.05 (1H, m), 6.53 (1H, d, J 9.6 Hz), 6.29 (1H, d, J 0.5 Hz), 5.88 (2H, s), 2.78 (3H, s). LCMS (ES$^+$) RT 3.12 minutes, 392 [$^{35}$Cl]:394 [$^{37}$Cl] 3:1 (M+H$^+$).

EXAMPLE 37

1-(3-Chlorobenzyl)-4-phenyl-2-(pyrrolidin-1-ylcarbonyl)-1,4-dihydro-5H-pyrrolo[3,2-b]pyridin-5-one From Intermediate 29 (400 mg, 1.00 mmol), using pyrrolidine (0.25 ml, 3.00 mmol), following the procedure of Example 35. Purification by chromatography (EtOAc, silica) gave the title compound (102 mg, 24%). $\delta_H$ (d$_3$-MeOD) 7.92 (1H, d, J, 9.6 Hz), 7.53-7.41 (3H, m), 7.34-7.31 (2H, m), 7.24-7.17 (2H, m), 7.07 (1H, s), 7.00-6.97 (1H, m), 6.44 (1H, d, J 9.6 Hz), 5.87 (1H, s), 5.45 (2H, s), 3.33 (2H, t, J 6.7 Hz), 3.13 (2H, t, J 6.7 Hz), 1.78-1.70 (2H, m), 1.64-1.57 (2H, m). LCMS (ES$^+$) RT 3.31 minutes, 432 [$^{35}$Cl]:434 [$^{37}$Cl] 3:1 (M+H$^+$).

EXAMPLE 38

1-(3-Chlorobenzyl)-5-oxo-4-phenyl-4,5-dihydro-1H-pyrrolo[3,2-b]pyridine-2-carbohydrazide A solution of Example 26 (200 mg, 0.49 mmol) in 2-ethoxyethanol (3 ml) was treated with hydrazine hydrate (0.10 ml, 2.04 mmol) and heated at 115° C. overnight. The reaction mixture was concentrated in vacuo. Purification by chromatography (10%-50% EtOAc in DCM, silica) gave the title compound (60 mg, 31%). $\delta_H$ (d$_3$-MeOD) 7.81 (1H, d, J 9.6 Hz), 7.55-7.41 (3H, m), 7.34-7.31 (2H, m), 7.21-7.13 (2H, m), 7.06 (1H, s), 6.99-6.95 (1H, m), 6.42 (1H, d, J 9.6 Hz), 6.17 (1H, s), 5.76 (2H, s). LCMS (ES$^+$) RT 2.78 minutes, 393 [$^{35}$Cl]:395 [$^{37}$Cl] 3:1 (M+H$^+$).

EXAMPLE 39

Ethyl 1-(3-chlorobenzyl)-4-(1H-indol-5-yl)-5-oxo-4,5-dihydro-1H-pyrrolo[3,2-b]pyridine-2-carboxylate From Intermediate 26 (500 mg, 1.51 mmol) and 5-indolylboronic acid (488 mg, 3.03 mmol) according to the procedure for Example 23. Purification by chromatography (10%-50% EtOAc in DCM, silica) gave the title compound (300 mg, 44%). $\delta_H$ (d$_3$-MeOD) 7.96 (1H, d, J 9.8 Hz), 7.51-7.48 (2H, m), 7.43-7.41 (1H, m), 7.33-7.26 (2H, m), 7.17 (1H, s), 6.98-6.92 (2H, m), 6.46-6.41 (2H, m), 6.05 (1H, s), 5.76 (2H, s), 4.09 (2H, q, J 7.1 Hz), 1.07 (3H, t, J 7.1 Hz). LCMS (ES$^+$) RT 3.62 minutes, 446 [$^{35}$Cl]:448 [$^{37}$Cl] 3:1 (M+H$^+$).

EXAMPLE 40

Ethyl 1-(3-chlorobenzyl)-5-oxo-4-(3-thienyl)-4,5-dihydro-1H-pyrrolo[3,2-b]pyridine-2-carboxylate From Intermediate 26 (500 mg, 1.51 mmol) and thiophene-3-boronic acid (388 mg, 3.03 mmol) according to the procedure for Example 23. Purification by chromatography (10%-50% EtOAc in DCM, silica) gave the title compound (100 mg, 16%). $\delta_H$ (d$_3$-MeOD) 7.44-7.38 (3H, m), 7.19-7.15 (3H, m), 7.00 (1H, s), 6.90-6.84 (1H, m), 6.53-6.41 (2H, m), 5.67 (2H, s), 4.21 (2H, q, J 7.1 Hz), 1.23 (3H, t, J 7.1 Hz). LCMS (ES$^+$) RT 3.80 minutes, 413 [$^{35}$Cl]:415 [$^{37}$Cl] 3:1 (M+H$^+$).

EXAMPLE 41

1-(3-Chlorobenzyl)-4-(1H-indol-5-yl)-5-oxo-4,5-dihydro-1H-pyrrolo[3,2-b]pyridine-2-carboxamide To a solution of Intermediate 30 (50 mg, 0.12 mmol) in DMF (1 ml) was added CDI (46 mg, 0.28 mmol) and the mixture stirred at r.t. for 1 h The solution was treated with 880 ammonia (0.5 ml) and stirred for a further 15 min. The reaction mixture was partitioned between DCM and water (10 nil each) and neutralised with 2M HCl (pH 7-8). The mixture was extracted with DCM (2×10 ml), dried (MgSO$_4$) and concentrated in vacuo. Purification by chromatography (5% MeOH in DCM, silica) gave the title compound (15 mg, 30%). $\delta_H$ (d$_3$-MeOD) 7.82 (1H, d J 9.6 Hz), 7.51-7.48 (2H, m), 7.30-7.25 (3H, m), 7.07 (1H, s), 7.00-6.95 (2H, m), 6.47-6.44 (2H, m), 6.28 (1H, s), 5.80 (2H, s). LCMS (ES$^+$) RT 2.95 minutes, 417 [$^{35}$Cl]:419 [$^{37}$Cl] 3:1 (M+H$^+$).

EXAMPLE 42

Ethyl 1-(4-fluoro-3-methylbenzyl)-5-oxo-4-phenyl-4,5-dihydro-1H-pyrrolo[3,2-b]pyridine-2-carboxylate From Intermediate 33 (680 mg, 2.07 mmol) and phenylboronic acid (488 mg, 4.00 mmol) according to the procedure for Example 23. Purification by chromatography (5%-30% EtOAc in DCM, silica) gave the title compound (531 mg, 64%). $\delta_H$ (CDCl$_3$) 7.86 (1H, d, J 9.7 Hz), 7.56-7.44 (3H, s), 7.31 (2H, d, J 7.1 Hz), 6.95 (1H, d, J 7.2 Hz), 6.89-6.83 (2H, m), 6.48 (1H, d, J 9.7 Hz), 6.19 (1H, s), 5.71 (2H, s), 4.16 (2H, q, J 7.1 Hz), 2.11 (3H, s), 1.16 (3H, t, J 7.1 Hz). LCMS (ES$^+$) RT 3.82 minutes, 405 (M+H$^+$).

EXAMPLE 43

1-(3-Chlorobenzyl)-4-(3-thienyl)-1,4-dihydro-5H-pyrrolo[3,2-b]pyridin-5-one

From Intermediate 35 (680 mg, 3.15 mmol) and 3-chlorobenzyl bromide (0.45 ml, 3.46 mmol) according to the procedure for Example 1. Purification by chromatography (10%40% EtOAc in DCM, silica) gave the title compound (843 mg, 79%). $\delta_H$ (CDCl$_3$) 7.46-7.50 (2H, m), 7.40 (1H, d, J 9.5 Hz), 7.33-7.31 (2H, m), 7.26 (1H, dd, J 1.5, 4.9 Hz), 7.15 (1H, s), 7.04-7.00 (1H, m), 6.95 (1H, d, J 3.0 Hz), 6.42 (1H, d, J 9.5 Hz), 5.91 (1H, d, J 3.0 Hz), 5.22 (2H, s). LCMS (ES$^+$) RT 3.32 minutes, 341 [$^{35}$Cl]:343 [$^{37}$Cl] 3:1 (M+H$^+$).

EXAMPLE 44

Ethyl 1-(3-chlorobenzyl)-4-(4-methylphenyl)-5-oxo-4,5-dihydro-1H-pyrrolo[3,2-b]pyridine-2-carboxylate From Intermediate 26 (350 mg, 1.06 mmol) and 4-methylphenylboronic acid (288 mg, 2.12 mmol), according to the procedure for Example 23. Purification by chromatography (10-15% EtOAc in DCM, silica) gave the title compound (328 mg, 74%). $\delta_H$ (CDCl$_3$) 7.41 (1H, d, J 9.7 Hz), 7.32-7.18 (6H, s), 7.00 (1H, s), 6.90-6.88 (1H, m), 6.55 (1H, d, J 9.7 Hz), 6.33 (1H, s), 5.67 (2H, s), 4.18 (2H, q, J 7.1 Hz), 2.39 (3H, s), 1.21 (3H, t, J 7.1 Hz). LCMS (ES$^+$) RT 3.96 minutes, 421 [$^{35}$Cl]:423 [$^{37}$Cl] 3:1 (M+H$^+$).

EXAMPLE 45

1-(2-Cyanobenzyl)-5-oxo-4-phenyl-4,5-dihydro-1H-pyrrolo[3,2-b]pyridine-2-carboxamide From Intermediate 40 (314 mg, 0.85 mmol) using 880 ammonia (2 ml), according to the procedure for Example 35. Purification by chromatography (EtOAc, silica) gave the title compound (100 mg, 32%). $\delta_H$ (d$_6$-DMSO) 7.75 (1H, d, J 9.7 Hz), 7.72-7.70 (2H, m), 7.47-7.24 (5H, m), 6.99 (1H, br s), 6.43-6.31 (2H, m), 6.21 (1H, d, J 9.7 Hz), 5.90 (2H, s). LCMS (ES$^+$) RT 2.71 minutes, 369 (M+H$^+$).

EXAMPLE 46

1-(4-Fluoro-3-methylbenzyl)-5-oxo-4-phenyl-4,5-dihydro-1H-pyrrolo[3,2-b]pyridine-2-carboxamide From Intermediate 41 (504 mg, 1.34 mmol) using 880 ammonia (2 ml), according to the procedure for Example 35. Purification by chromatography (EtOAc, silica) gave the title compound (220 mg, 44%). $\delta_H$ (d$_6$-DMSO) 7.85 (1H, d, J 9.7 Hz), 7.59-7.40 (3H, m), 7.34-7.31 (2H, m), 7.08-7.03 (1H, m), 6.99 (1H, d, J 9.7 Hz), 6.92-6.87 (1H, m), 6.31 (1H, s), 6.29 (1H, d, J 9.7 Hz), 5.75 (2H, s), 2.11 (3H, s). LCMS (ES$^+$) RT 2.95 minutes, 376 (M+H$^+$).

EXAMPLE 47

1-(3-Chlorobenzyl)-4-(4-methylphenyl)-5-oxo-4,5-dihydro-1H-pyrrolo[3,2-b]pyridine-2-carboxamide From Intermediate 42 (278 mg, 0.71 mmol) using 880 ammonia (2 ml), according to the procedure for Example 35. Purification by chromatography (20% EtOAc in DCM to neat EtOAc, silica) gave the title compound (168 mg, 74%). $\delta_H$ (d$_6$-DMSO) 7.93-7.86 (1H, br m), 7.39-7.23 (6H, m), 7.19 (1H, s), 7.07-7.01 (1H, m), 6.39 (1H, s), 6.32 (1H, d, J 9.6 Hz), 5.84 (2H, s), 2.37 (3H, s). LCMS (ES$^+$) RT 3.06 minutes, 392[$^{35}$Cl]:394 [$^{37}$Cl] 3:1 (M+H$^+$).

EXAMPLE 48

1-(3-Chlorobenzyl)-4-(4-methylphenyl)-5-oxo-4,5-dihydro-1H-pyrrolo[3,2-b]pyridine-2-carbohydrazide From Example 44 (278 mg, 0.71 mmol) using hydrazine hydrate (3 ml), according to the procedure for Example 38. Purification by trituration with DCM gave the title compound (168 mg, 74%). $\delta_H$ (d$_6$-DMSO) 7.96 (1H, d, J 9.7 Hz), 7.37-7.25 (6H, m), 7.19 (1H, s), 7.00 (1H, d, J 6.4 Hz), 6.44 (1H, s), 6.40 (1H, d, J 9.7 Hz), 5.82 (2H, s), 2.33 (3H, s). LCMS (ES$^+$) RT 2.93 minutes, 407 [$^{35}$Cl]:409 [$^{37}$Cl] 3:1 (M+H$^+$).

EXAMPLE 49

Ethyl 1-(3-chlorobenzyl)-4-(2-nitrophenyl)-5-oxo-4,5-dihydro-1H-pyrrolo[3,2-b]pyridine-2-carboxylate A suspension of Intermediate 26 (1.60 g, 4.85 mmol) in DMF (15 ml) was treated with sodium hydride (60% in mineral oil, 240 mg, 5.82 mmol) and stirred at r.t. for 20 mins. 2-Fluoronitrobenzene (1.02 ml, 9.70 mmol) was added and the reaction heated at 90° C. for 3 days. The reaction mixture was concentrated in vacuo, partitioned between EtOAc (100 ml) and water (50 ml) and extracted with EtOAc (50 ml). The combined organics were washed with brine, dried (MgSO$_4$) and concentrated in vacuo. Purification by chromatography (10%-15% EtOAc in DCM, silica) gave the title compound (120 mg, 5%). $\delta_H$ (CDCl$_3$) 8.17 (1H, d, J 8.0 Hz), 7.80-7.75 (1H, m), 7.65-7.60 (1H, m), 7.51 (1H, d, J, 8.0 Hz), 7.47 (1H, d, J 9.8 Hz), 7.23-7.20 (2H, m), 7.03 (1H, s), 6.88-6.84 (1H, m), 6.50 (1H, d, J 9.8 Hz), 6.29 (1H, s), 5.85 (1H, d, J 16.2 Hz), 5.54 (1H, d, J 16.2 Hz), 4.19 (2H, q, J 7.0 Hz), 1.21 (3H, t, J 7.0 Hz). LCMS (ES$^+$) RT 3.68 minutes, 452 [$^{35}$Cl]:454 [$^{37}$Cl] 3:1 (M+H$^+$).

EXAMPLE 50

1-(1,3-Benzothiazol-2-ylmethyl)-4-phenyl-1,4-dihydro-5H-pyrrolo[3,2-b]pyridin-5-one From Intermediate 5 (100 mg, 0.48 mmol) using 2-(bromomethyl)-1,3-benzothiazole (119 mg, 0.52 mmol) according to the procedure for Example 33. Purification by chromatography (50% EtOAc in DCM to neat EtOAc, silica) gave the title compound (80 mg, 50%). $\delta_H$ (CDCl$_3$) 7.98 (1H, d, J 8.7 Hz), 7.78 (1H, d, J 7.5 Hz), 7.54-7.34 (8H, m), 6.97 (1H d, J 3.1 Hz), 6.40 (1H, d, J 9.5 Hz), 5.67 (1H, d, J 3.1 Hz), 5.54 (2H, s). LCMS (ES$^+$) RT 3.17 minutes, 358 (M+H$^+$).

EXAMPLE 51

1-[(5-Chloro-2-thienyl)methyl]-4-phenyl-1,4-dihydro-5H-pyrrolo[3,2-b]pyridin-5-one From Intermediate 5 (100 mg, 0.48 mmol) using 2-chloro-5-(chloromethyl)-thiophene (0.063 ml, 0.52 mmol) according to the procedure for Example 33. Purification by chromatography (50% EtOAc in DCM, silica) gave the title compound (150 mg, 92%). $\delta_H$ (CDCl$_3$) 7.50-7.32 (6H, m), 6.82 (1H, d, J 3.0 Hz), 6.73-6.68 (2H, m), 6.40 (1H, d, J 9.5

Hz), 5.58 (1H, d, J 3.0 Hz), 5.19 (2H, s). LCMS (ES⁺) RT 3.35 minutes, 341 [³⁵Cl]:343 [³⁷Cl] 3:1 (M+H⁺).

EXAMPLE 52

1-Benzyl-4-phenyl-3-(trifluoroacetyl)-1,4-dihydro-5H-pyrrolo[3,2-b]pyridin-5-one From Intermediate 45 (280 mg, 0.86 mmol) using copper (II) acetate (26 mg, 0.13 mmol), pyridine (0.25 ml, 2.50 mmol), pyridine N-oxide (238 mg, 2.50 mmol) and phenylboronic acid (391 mg, 2.50 mmol) according to the procedure for Example 23. Purification by chromatography (EtOAc, silica) gave the title compound (77 mg, 22%). $\delta_H$ (d$_6$-DMSO): 8.42-8.43 (1H, m), 7.93 (1H, d, J 9.7 Hz), 7.44-7.32 (8H, m), 7.24-7.21 (2H, m), 6.40 (1H, d, J 9.7 Hz), 5.58 (2H, s). LCMS (ES⁺) RT 3.46 minutes, 397 (M+H⁺).

EXAMPLE 53

2-{[(2S)-2-(Hydroxymethyl)pyrrolidin-1-yl]carbonyl}-1-(3-methylbenzyl)-4-phenyl-1,4-dihydro-5H-pyrrolo[3,2-b]pyridin-5-one A suspension of Intermediate 28 (400 mg, 1.04 mmol) in DCM (20 ml) was treated with EDC (403 mg, 2.10 mmol) and HOBT (284 mg, 2.10 mmol) and stirred at r.t. for 1 h. (S)-Prolinol (0.21 ml, 2.10 mmol) was added and the reaction was stirred at r.t. overnight. The reaction mixture was diluted with DCM (20 ml), washed with water, dried (Na$_2$SO$_4$) and concentrated in vacuo. Purification by chromatography (EtOAc, silica) gave the title compound (118 mg, 25%). $\delta_H$ (CDCl$_3$, 380K) 7.88 (1H, d, J 9.6 Hz), 7.56 (2H, m), 7.47 (1H, m), 7.39 (2H, m), 7.21 (1H, d, J 7.7 Hz), 7.09 (1H, m), 7.02 (1H, s), 6.96 (1H, d, J 7.7 Hz), 6.30 (1H, d, J 9.6 Hz), 5.84 (1H, s), 5.48 (1H, d, J 15.7 Hz), 5.42 (1H, d, J 15.7 Hz), 4.03 (1H, br s), 3.44-3.42 (1H, m), 3.37-3.36 (1H, m), 3.33-3.28 (2H, m), 2.29 (3H, s), 1.84-1.75 (3H, m), 1.57-1.55 (1H, m). LCMS (ES⁺) RT 2.40 minutes, 442 (M+H⁺).

Biological Assays

The following assays and animal models can be used to demonstrate the potency and selectivity of the compounds according to the invention. In each assay an IC$_{50}$ value was determined for each test compound and represents the concentration of compound necessary to achieve 50% inhibition.

Preparation of Activated Human p38α for Inhibitor Assays

Purification of human p38α

Human p38α, incorporating an N-terminal (His)$_6$ tag, was expressed in baculovirus-infected High-Five™ cells (Invitrogen) according to the manufacturer's instructions. The cells were harvested 72 h post-infection and lysed in phosphate-buffered saline (PBS) containing 1% (w/v) β-octylglucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after awash with 15 mM imidazole in PBS) and directly applied to a HiTrap Q™ column (AP Biotech). Bound protein was eluted using a 20 column volume, 0 to 1 M NaCl gradient. Fractions containing (His)6-p38 were aliquoted and stored at −70° C. prior to their activation.

Preparation of GST-MKK6EE-Containing Lysates

*E. coli* (BL21 pLysS) expressing the constitutively-activated form of human MKK6 fused with an N-terminal glutathione-S-transferase tag (GST-MKK6EE) were harvested by centrifugation and frozen at −70° C. Cells were lysed by resuspension in ¹/₁₀th the culture volume of PBS containing Complete, EDTA-free™ protease inhibitors followed by sonication on ice for 4×15 sec. Cell debris was removed by centrifugation at 35,000×g and the resultant supernatant stored in aliquots at −70° C.

Activation of (His)6-p38

0.45 ml of purified (His)6-p38 was incubated with 50 µl of the GST-MKK6EE-containing lysate for 30 min at 23° C. in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6-p38 preparation. The activated (His) 6-p38 was then diluted×10 in PBS and repurified using the method described above. The concentration of purified, activated (His)6-p38 was measured by UV absorbance at 280 nm using A280, 0.1%=1.2 and the preparation stored in aliquots at −70° C. prior to its use in inhibitor assays.

p38 Inhibition Assays

Inhibition of Phosphorylation of Biotinylated Myelin Basic Protein (MBP)

The inhibition of p38-catalysed phosphorylation of biotinylated MBP is measured using a DELFIA-based format. The assay was performed in a buffer comprising 20 mM HEPES (pH 7.4), 5 mM MgCl$_2$ and 3 mM DTT. For a typical IC$_{50}$ determination, biotinylated MBP (2.5 µM) was incubated at room temperature in a streptavidin-coated microtitre plate together with activated gst-p38 (10 nM) and ATP (1 µM in the presence of a range of inhibitor concentrations (final concentration of DMSO is 2 percent). After fifteen minutes the reaction was terminated by the addition of EDTA (75 mM). The microtitre plate was then washed with Tris-buffered saline (TBS), prior to the addition of 100 µl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature. IC$_{50}$ values are determined from the plot of log$_{10}$[inhibitor concentration] (x-axis) versus percentage inhibition of the fluorescence generated by a control sample in the absence of inhibitor (y-axis).

Purification of Human Peripheral Blood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400×g for 35 min over a Ficoll-paque gradient (Amersham-Pharmacia Biotech, UK). Cells at the interface were removed and washed once followed by a low speed spin (250×g) to remove platelets. Cells were then resuspended in DMEM containing 10% FCS, penicillin 100 units ml⁻¹, streptomycin 50 µg ml⁻¹ and glutamine 2 mM (Gibco, UK).

Inhibitor Dilutions

Inhibitor stocks (20 mM) were kept as a frozen solution (−20° C.) in DMSO. Serial dilutions of inhibitor were performed in DMSO as 250-times concentrated stocks. Inhibitors were diluted 1 in 250 into tissue culture media, pre-warmed to 37° C. and transferred to plates containing PBMC.

PBMC and inhibitors were incubated together for 30 min prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 µl. Inhibitor was incubated with whole blood for 30 min prior to the addition of LPS.

LPS Stimulation of PBMC

PBMC were resuspended at a density of $2\times10^5$ cells/well in flat-bottomed 96-well tissue culture treated plates. After the addition of inhibitor cells were stimulated with an optimal dose of LPS (*E. coli* strain B5:055, Sigma, at a final concentration of 1 µgml$^{-1}$) and incubated at 37° C. in 5% $CO_2$/95% air for 18 hours. TNF-α levels were measured from cell-free supernatants by sandwich ELISA (BioSource #CHC1751).

LPS Stimulation of Whole Blood

Whole blood was taken by venous puncture using heparinised vacutainers (Becton Dickinson), and 500 µl of blood aliquoted into each well of a 24-well tissue culture treated plate. After the addition of inhibitor cells were stimulated with an optimal dose of LPS (*E. coli* strain B5:055, Sigma, at a final concentration of 1 µgml$^{-1}$) and incubated at 37° C. without $CO_2$ for 18 hours. TNF-α levels were measured from cell-free supernatants by sandwich ELISA (BioSource #CHC1751).

Rat LPS-Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNF-α by commercial ELISA.

Rat CIA

Female Lewis rats (180-200 g) are anaesthetised with Isofluor and immunised i.d. at the base of the tail with 2×100 µl of emulsion containing 4 mg/ml bovine collagen II in 0.01 M acetic acid and Freund's Incomplete Adjuvant at a ratio of 1:1. A polyarthritis develops with onset from about 13 days post-sensitisation. The disease is mainly confined to the ankles and is quantified by plethysmometry. Results are expressed as change in paw volume over time.

CONCLUSION

In the p38 inhibitor assays described above, the compounds of the Examples have $IC_{50}$ values of around 2 µM and below. The compounds of the invention are clearly potent inhibitors of p38 kinase, especially p38α kinase.

The invention claimed is:
1. A compound of formula (1):

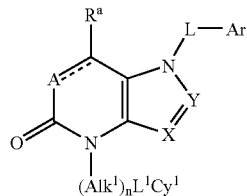

(1)

wherein:
the dashed line joining A and C(R$^a$) is present and represents a bond and A is a —C(R$^b$)= group;

R$^a$ and R$^b$ are each hydrogen;
X is a —CH= group;
Y is a —C(R$^e$)= group;
R$^e$ is hydrogen, —CN, —COR$^1$, —CO$_2$R$^1$, —CONR$^{1a}$R$^{2a}$, —S(O)$_2$NR$^{1a}$R$^{2a}$, —CONR$^{1a}$OR$^{2a}$ or —C(O)N(R$^{3a}$)NR$^{1a}$R$^{2a}$;
R$^1$ is methyl, ethyl or trifluoromethyl
R$^{1a}$ and R$^{2a}$ are, independently, a hydrogen atom or methyl group, or together with the nitrogen atom to which they are attached, represent —(CH$_2$)$_4$— or —CH(CH$_2$OH) (CH$_2$)$_3$—;
R$^{3a}$ is a hydrogen atom or C$_{1-6}$alkyl group;
L is a —CH$_2$—, —CH(CH$_3$)—, —C(O)— or —CH$_2$CH$_2$— group;
n is zero;
Alk$^1$ is an optionally substituted aliphatic or heteroaliphatic chain;
L$^1$ is a covalent bond;
Cy$^1$ is phenyl, methylphenyl, methoxyphenyl, thienyl or indolyl; and
Ar represents phenyl, pyridinyl, thienyl or benzothienyl, any of which groups may be optionally substituted by one or two substituents selected from halogen, cyano, C$_{1-6}$ alkyl, C$_{1-6}$ alkoxy and nitro;
or a pharmaceutically acceptable salt or N-oxide thereof.

2. A compound as claimed in claim 1 wherein Ar is a phenyl, fluorophenyl, difluorophenyl, chlorophenyl, dichlorophenyl, (chloro)(fluoro)phenyl, cyanophenyl, methylphenyl, (fluoro)(methyl)phenyl, methoxyphenyl, nitrophenyl, pyridinyl, chlorothienyl or benzothienyl group.

3. A compound as claimed in claim 1 which is
1-Benzyl-4-phenyl-1,4-dihydro-5H-pyrrolo[3,2-b]pyridin-5-one;
1-(3-Chlorobenzyl)-4-phenyl-1,4-dihydro-5H-pyrrolo[3,2-b]pyridin-5-one;
1-(4-Fluorobenzyl)-4-phenyl-1,4-dihydro-5H-pyrrolo[3,2-b]pyridin-5-one;
1-(2,6-Dichlorobenzyl)-4-phenyl-1,4-dihydro-5H-pyrrolo[3,2-b]pyridin-5-one;
1-(3-Methoxybenzyl)-4-phenyl-1,4-dihydro-5H-pyrrolo[3,2-b]pyridin-5-one;
1-Benzyl-4-(4-methoxyphenyl)-1,4-dihydro-5H-pyrrolo[3,2-b]pyridin-5-one;
1-Benzoyl--4-phenyl-1,4-dihydro-5H-pyrrolo[3,2-b]pyridin-5-one;
4-[(5-Oxo-4-phenyl-4,5-dihydro-1H-pyrrolo[3,2-b]pyridin-1-yl)methyl]benzonitrile;
3-[5-Oxo-4-phenyl-4,5-dihydro-1H-pyrrolo[3,2-b]pyridin-1-yl)methyl]benzonitrile;
1-(2-Methylbenzyl)-4-phenyl-1,4-dihydro-5H-pyrrolo[3,2-b]pyridin-5-one;
1-(3-Methylbenzyl)-4-phenyl-1,4-dihydro-5H-pyrrolo[3,2-b]pyridin-5-one;
1-(4-Methylbenzyl)-4-phenyl-1,4-dihydro-5H-pyrrolo[3,2-b]pyridin-5-one;
1-(4-Chlorobenzyl)-4-phenyl-1,4-dihydro-5H-pyrrolo[3,2-b]pyridin-5-one;
1-(3,4-Dichlorobenzyl)-4-phenyl-1,4-dihydro-5H-pyrrolo[3,2-b]pyridin-5-one;
1-(2,5-Dichlorobenzyl)-4-phenyl-1,4-dihydro-5H-pyrrolo[3,2-b]pyridin-5-one;
1-(3,4-Difluorobenzyl)-4-phenyl-1,4-dihydro-5H-pyrrolo[3,2-b]pyridin-5-one;
1-(2,4-Difluorobenzyl)-4-phenyl-1,4-dihydro-5H-pyrrolo[3,2-b]pyridin-5-one;
1-(3-Chloro-4-fluorobenzyl)-4-phenyl-1,4-dihydro-5H-pyrrolo[3,2-b]pyridin-5-one;

4-Phenyl-1-(pyridin-4-ylmethyl)-1,4-dihydro-5H-pyrrolo[3,2-b]pyridin-5-one;
4-Phenyl-1-(pyridin-3-ylmethyl)-1,4-dihydro-5H-pyrrolo[3,2-b]pyridin-5-one;
4-Phenyl-1-(1-phenylethyl)-1,4-dihydro-5H-pyrrolo[3,2-b]pyridin-5-one;
1-(3-Chlorobenzyl)-4-phenyl-2-(pyrrolidin-1-ylsulfonyl)-1,4-dihydro-5H-pyrrolo[3,2-b]pyridin-5-one;
Ethyl 1-benzyl-5-oxo-4-phenyl-4,5-dihydro-1H-pyrrolo[3,2-b]pyridine-2-carboxylate;
Ethyl 1-(3-chloro-4-fluorobenzyl)-5-oxo-4-phenyl-4,5-dihydro-1H-pyrrolo[3,2-b]pyridine-2-carboxylate;
Ethyl 1-(3-methylbenzyl)-5-oxo-4-phenyl-4,5-dihydro-1H-pyrrolo[3,2-b]pyridine-2-carboxylate;
Ethyl 1-(3-chlorobenzyl)-5-oxo-4-phenyl-4,5-dihydro-1H-pyrrolo[3,2-b]pyridine-2-carboxylate;
1-(3-Chloro-4-fluorobenzyl)-N-methoxy-N-methyl-5-oxo-4-phenyl-4,5-dihydro-1H-pyrrolo[3,2-b]pyridine-2-carboxamide;
N-Methoxy-N-methyl-1-(3-methylbenzyl)-5-oxo-4-phenyl-4,5-dihydro-1H-pyrrolo[3,2-b]pyridine-2-carboxamide;
1-(3-Chlorobenzyl)-N-methoxy-N-methyl-5-oxo-4-phenyl-4,5-dihydro-1H-pyrrolo[3,2-b]pyridine-2-carboxamide;
1-(3-Chloro-4-fluorobenzyl)-5-oxo-4-phenyl-4,5-dihydro-1H-pyrrolo[3,2-b]pyridine-2-carboxamide;
1-(3-Methylbenzyl)-5-oxo-4-phenyl-4,5-dihydro-1H-pyrrolo[3,2-b]pyridine-2-carboxamide;
1-(3-Chlorobenzyl)-5-oxo-4-phenyl-4,5-dihydro-1H-pyrrolo[3,2-b]pyridine-2-carboxamide;
4-Phenyl-1-(2-phenylethyl)-1,4-dihydro-5H-pyrrolo[3,2-b]pyridin-5-one;
1-(3-Chlorobenzyl)-5-oxo-4-phenyl-4,5-dihydro-1H-pyrrolo[3,2-b]pyridine-2-carbonitrile;
1-(3-Chlorobenzyl)-N,N-dimethyl-5-oxo-4-phenyl-4,5-dihydro-1H-pyrrolo[3,2-b]pyridine-2-carboxamide;
1-(3-Chlorobenzyl)-N-methyl-5-oxo-4-phenyl-4,5-dihydro-1H-pyrrolo[3,2-b]pyridine-2-carboxamide;
1-(3-Chlorobenzyl)-4-phenyl-2-(pyrrolidin-1-ylcarbonyl)-1,4-dihydro-5H-pyrrolo[3,2-b]pyridin-5-one;
1-(3-Chlorobenzyl)-5-oxo-4-phenyl-4,5-dihydro-1H-pyrrolo[3,2-b]pyridine-2-carbohydrazide;
Ethyl 1-(3-chlorobenzyl)-4-(1H-indol-5-yl)-5-oxo-4,5-dihydro-1H-pyrrolo[3,2-b]pyridine-2-carboxylate;
Ethyl 1-(3-chlorobenzyl)-5-oxo-4-(3-thienyl)-4,5-dihydro-1H-pyrrolo[3,2-b]pyridine-2-carboxylate;
1-(3-Chlorobenzyl)-4-(1H-indol-5-yl)-5-oxo-4,5-dihydro-1H-pyrrolo[3,2-b]pyridine-2-carboxamide;
Ethyl 1-(4-fluoro-3-methylbenzyl)-5-oxo-4-phenyl-4,5-dihydro-1H-pyrrolo[3,2-b]pyridine-2-carboxylate;
1-(3-Chlorobenzyl)-4-(3-thienyl)-1,4-dihydro-5H-pyrrolo[3,2-b]pyridin-5-one;
Ethyl 1-(3-chlorobenzyl)-4-(4-methylphenyl)-5-oxo-4,5-dihydro-1H-pyrrolo[3,2-b]pyridine-2-carboxylate;.
1-(2-Cyanobenzyl)-5-oxo-4-phenyl-4,5-dihydro-1H-pyrrolo[3,2-b]pyridine-2-carboxamide;
1-(4-Fluoro-3-methylbenzyl)-5-oxo-4-phenyl-4,5-dihydro-1H-pyrrolo[3,2-b]pyridine-2-carboxamide;
1-(3-Chlorobenzyl)-4-(4-methylphenyl)-5-oxo-4,5-dihydro-1H-pyrrolo[3,2-b]pyridine-2-carboxamide;
1-(3-Chlorobenzyl)-4-(4-methylphenyl)-5-oxo-4,5-dihydro-1H-pyrrolo[3,2-b]pyridine-2-carbohydrazide;
Ethyl 1-(3-chlorobenzyl)-4-(2-nitrophenyl)-5-oxo-4,5-dihydro-1H-pyrrolo[3,2-b]pyridine-2-carboxylate;
1-(1,3-Benzothiazol-2-ylmethyl)-4-phenyl-1,4-dihydro-5H-pyrrolo[3,2-b]pyridin-5-one;
1 [(5-Chloro-2-thienyl)methyl]-4-phenyl-1,4-dihydro-5H-pyrrolo[3,2-b]pyridin-5-one;
1-Benzyl-4-phenyl-3-(trifluoroacetyl)-1,4-dihydro-5H-pyrrolo[3,2-b]pyridin-5-one; or
2-{[(2S)-2-(Hydroxymethyl)pyrrolidin-1-yl]carbonyl}-1-(3-methylbenzyl)-4-phenyl-1,4-dihydro-5H-pyrrolo[3,2-b]pyridin-5-one.

4. A pharmaceutical composition comprising a compound as claimed in claim 1, or a pharmaceutically acceptable salt, or N-oxide thereof, in association with a pharmaceutically acceptable carrier.

\* \* \* \* \*